(12) United States Patent
Kikuchi et al.

(10) Patent No.: US 6,254,540 B1
(45) Date of Patent: Jul. 3, 2001

(54) ULTRASONIC IMAGE PROCESSING APPARATUS FOR CONSTRUCTING THREE-DIMENSIONAL IMAGE USING VOLUME-RENDERING DATA AND SURFACE-RENDERING DATA SIMULTANEOUSLY

(75) Inventors: Hayato Kikuchi, Hachioji (JP); Rich Didday, Soquel; Hong Q. Zhao, San Jose, both of CA (US)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/444,009

(22) Filed: Nov. 19, 1999

(51) Int. Cl.[7] ........................................................ A61B 8/00
(52) U.S. Cl. ........................................... 600/443; 128/916
(58) Field of Search ........................... 600/443, 447, 600/448, 449, 437, 407, 408; 128/916

(56) References Cited

U.S. PATENT DOCUMENTS

| | | | |
|---|---|---|---|
| 5,706,816 | * | 1/1998 | Mochizuki et al. .................. 600/443 |
| 5,771,895 | | 6/1998 | Slager . |
| 6,083,162 | * | 7/2000 | Vining ................................. 600/407 |
| 6,116,244 | * | 9/2000 | Hossack et al. ..................... 128/916 |

* cited by examiner

Primary Examiner—Peter Vo
Assistant Examiner—Maulin Patel
(74) Attorney, Agent, or Firm—Ostrolenk, Faber, Gerb & Soffen, LLP

(57) ABSTRACT

An ultrasonic image processing apparatus includes an ultrasonic image input unit, an oblique image rendering unit, a surface extracting unit, a three-dimensional image rendering unit, an image synthesizing unit, and a monitor. The ultrasonic image input unit inputs ultrasonic image data from an ultrasonic probe that is inserted into a body cavity for transmitting or receiving ultrasonic waves. The oblique image rendering unit produces an oblique image. The surface extracting unit extracts surface data from the oblique image (boundary between a tissue and lumen). The three-dimensional image rendering unit produces three-dimensional images using volume-rendering data and surface-rendering data respectively. The image synthesizing unit reads the three-dimensional images produced by the three-dimensional image rendering unit and synthesizes the three-dimensional image of volume-rendering data and the three-dimensional image of surface-rendering data. The monitor displays a three-dimensional image produced by the image synthesizing unit.

21 Claims, 19 Drawing Sheets

ULTRASONIC IMAGE PROCESSING APPARATUS FOR CONSTRUCTING THREE-DIMENSIONAL IMAGE USING VOLUME-RENDERING DATA AND SURFACE-RENDERING DATA SIMULTANEOUSLY

BACKGROUND OF THE INVENTION

1. Field of the Invention

The present invention relates to an ultrasonic image processing apparatus for processing ultrasonic data to construct a three-dimensional image.

2. Description of the Related Art

Diagnostic ultrasound systems for ultrasonically scanning an intracavitary region using an ultrasonic probe so as to produce tomographic images of the region and its surroundings have been widely adopted these days.

Conventional ultrasonic probes can only provide linear scan-mode images and radial scan-mode images mutually independently from each other. In recent years, a proposal has been made for an ultrasonic probe which is capable of scanning a region three-dimensionally to thus assist in the grasping of tissue the size of a tumor or the like growing in a subject as disclosed, in, for example, Japanese Unexamined Patent Publication No. 62-219076 or 62-194310.

Using such an ultrasonic probe capable of scanning a region three-dimensionally, the size or area of a tumor or the like can be grasped and the volume thereof can be measured.

On the other hand, general personal computers are presently capable of handling complex image processing owing to the recent technological advances in performance.

However, Japanese Unexamined Patent Publication No. 62-219076 has a drawback. That is to say, since transmittance cannot be set mutually independently for a surface rendering mode and a volume rendering mode, information of minute irregularities on the surface of an intracavitary wall and information of an organ or the like inside the wall cannot be obtained readily and concurrently.

Similarly, while Japanese Unexamined Patent Publication No. 62-194310 has the advantage that an organ can be identified easily in a tomographic image, there is a drawback in that information of minute irregularities on the surface of an intracavitary wall and information of an organ or the like inside the wall cannot be readily and concurrently obtained from a three-dimensional image (stacked data).

SUMMARY OF THE INVENTION

An object of the present invention is to provide an ultrasonic image processing apparatus capable of simultaneously constructing a three-dimensional image using surface-rendering data and volume-rendering data in combination. Herein, transmittance can be set mutually independently for a surface rendering mode and a volume rendering mode. Information of minute irregularities on the surface of an intracavitary wall and information of an organ or the like inside the wall can be obtained readily and concurrently.

Another object of the present invention is to provide an ultrasonic image processing apparatus capable of coloring a three-dimensional image (stacked data). Herein, minute irregularities on the surface of an intracavitary wall or an organ or the like inside the wall, of which identification is hard to do using a gray-scale imaging mode alone, can be identified readily.

An ultrasonic image processing apparatus in accordance with the present invention includes an ultrasonic data acquiring means, an oblique image producing means, and a three-dimensional image rendering means. The ultrasonic data acquiring means acquires ultrasonic data of an intracavitary region. An oblique image is created by computing the two dimensional projection of rectilinear subregion of the three-dimensional stacked data set. The three-dimensional image rendering means extracts section data of the oblique image and ultrasonic data of the intracavitary wall so as to produce a three-dimensional image.

Other features and advantages of the present invention will be fully apparent from the description below.

BRIEF DESCRIPTION OF THE DRAWINGS

FIG. 1 shows the configuration of an ultrasonic image processing apparatus;

FIG. 2 is a flowchart describing a sequence followed by the ultrasonic image processing apparatus shown in FIG. 1;

FIG. 3 is an explanatory diagram for explaining a retrieval dialog box mentioned in the flowchart of FIG. 2;

FIG. 4 is an explanatory diagram for explaining a loading dialog box mentioned in the flowchart of FIG. 2;

FIG. 5 is an explanatory diagram for explaining a radial image mentioned in the flowchart of FIG. 2;

FIG. 6 is an explanatory diagram for explaining a DPR image mentioned in the flowchart of FIG. 2;

FIG. 7 is an explanatory diagram for explaining an image rotation as mentioned in the flowchart of FIG. 2;

FIG. 8 is an explanatory diagram for explaining a variation of the image rotation mentioned in the flowchart of FIG. 2;

FIG. 9 is an explanatory diagram for explaining a mode selection dialog box mentioned in the flowchart of FIG. 2;

FIG. 10 shows a concurrent display of a radial image, longitudinal images, and an oblique image rendering sections using texture data which are mentioned in the flowchart of FIG. 2;

FIG. 11 shows a concurrent display of a radial image, longitudinal images, and a three-dimensional image rendering sections using texture data and an intracavitary wall using surface-rendering data which are mentioned in the flowchart of FIG. 2;

FIG. 12 is a flowchart describing the sequence of animated image display mentioned in the flowchart of FIG. 2;

FIG. 13 is an explanatory diagram for explaining an oblique image shown in FIG. 10;

FIG. 14 is an explanatory diagram for explaining a three-dimensional image (stacked data) shown in FIG. 11;

FIG. 15 is an explanatory diagram for explaining the process of extracting data of the surface of an intracavitary wall from the three-dimensional image (stacked data) shown in FIG. 14;

FIG. 16 is the first flowchart describing the sequence of extracting data of the surface of an intracavitary wall from the three-dimensional image (stacked data) shown in FIG. 14;

FIG. 17 is the second flowchart describing the sequence of extracting data of the surface of an intracavitary wall from the three-dimensional image shown in FIG. 14;

FIG. 18 is the first explanatory diagram for explaining how to change planes for selecting a subregion of the three-dimensional image (stacked data) shown in FIG. 14; and FIG. 19 is the second explanatory diagram for explaining how to change planes for selecting a subregion of the three-dimensional image (stacked data) shown in FIG. 14.

FIG. 20 shows the configuration of an ultrasonic image processing apparatus;

FIG. 21 is a first explanatory diagram for explaining the operations performed by the ultrasonic image processing apparatus shown in FIG. 20; and FIG. 22 is a second explanatory diagram for explaining the operations performed by the ultrasonic image processing apparatus shown in FIG. 20.

FIG. 23 shows the configuration of an ultrasonic image processing apparatus; and FIG. 24 is an explanatory diagram for explaining the operations performed by the ultrasonic image processing apparatus shown in FIG. 24.

FIG. 25 shows the configuration of an ultrasonic image processing apparatus;

FIG. 26 is a first explanatory diagram for explaining the operations performed by the ultrasonic image processing apparatus shown in FIG. 25; and FIG. 27 is a second explanatory diagram for explaining the operations performed by the ultrasonic image processing apparatus shown in FIG. 25.

DESCRIPTION OF THE PREFERRED EMBODIMENTS

First Embodiment:

(Constituent Features)

Figure 1:
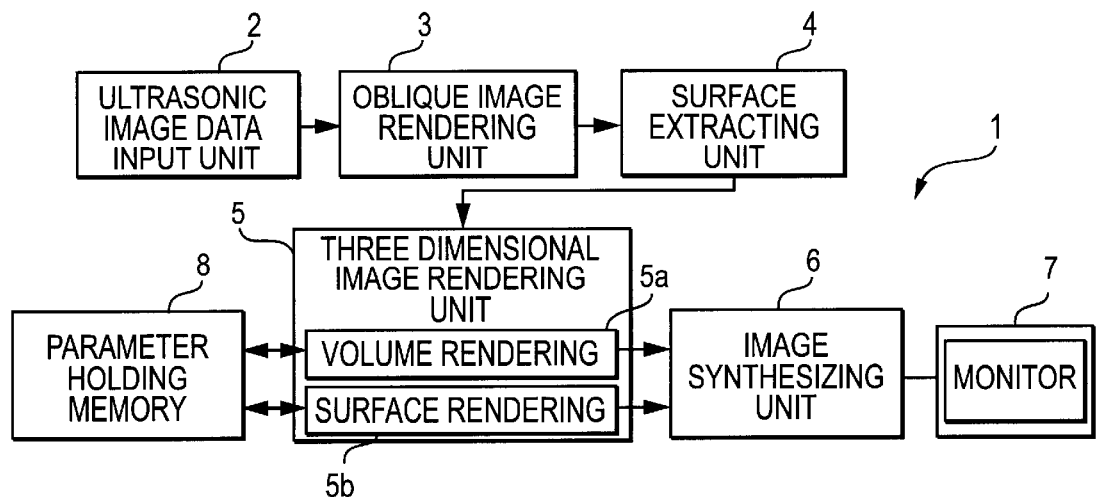
FIGS. 1 to FIG. 19 relate to the first preferred embodiment.

As shown in FIG. 1, an ultrasonic image processing apparatus 1 in accordance with the first embodiment of the present invention includes an ultrasonic image input unit 2, an oblique image rendering unit 3, a surface extracting unit 4, a three-dimensional image rendering unit 5, an image synthesizing unit 6, and a monitor 7. The ultrasonic image input unit 2 inputs ultrasonic image data from an ultrasonic probe (not shown) that is inserted into a body cavity for transmitting or receiving ultrasonic waves. The oblique image rendering unit 3 produces an oblique image. The surface extracting unit 4 extracts data of the surface of an intracavitary wall (boundary between a tissue and lumen) from the oblique image. The three-dimensional image rendering unit 5 produces three-dimensional images using volume-rendering data and surface-rendering data respectively. The image synthesizing unit 6 reads three-dimensional images produced by the three-dimensional image of volume-rendering unit 5 and synthesizes the three-dimensional image of volume-rendering data and the three-dimensional image of surface-rendering data. The monitor 7 displays a three-dimensional image produced by the image synthesizing unit 6.

Moreover, the three-dimensional image rendering unit 5 includes a volume-mode image rendering block 5a for producing a three-dimensional image (stacked data) using volume-rendering data, and a surface-mode image rendering block 5b for producing a three-dimensional image using surface-rendering data. An angle of display at which the images are displayed, positions and angles of sections rendered in the images, and other parameters are held in a parameter holding memory 8. The three-dimensional image rendering unit 5 has a memory in which produced three-dimensional image data is stored, though the memory is not shown. The image synthesizing unit 6 reads the (stacked) three-dimensional image data from the memory in the three-dimensional image rendering unit 5 and produces a synthetic three-dimensional image.

(Operations)

The ultrasonic image processing apparatus 1 having the foregoing components will be described below.

In the ultrasonic image processing apparatus 1, a plurality of ultrasonic tomographic image data items is input from the ultrasonic image input image 2. The oblique image constructing unit 3 uses the data items to produce an oblique image. The surface extracting unit 4 extracts data of a surface (a boundary between a tissue and lumen). The volume-mode image rendering block 5a of the three-dimensional image rendering unit 5 produces a three-dimensional image using volume-rendering data, while the surface-mode image rendering block 5b thereof produces a three-dimensional image using surface-rendering data. Coordinates indicating an angle of display at which the three-dimensional images are displayed, coordinates indicating positions and angles of sections rendered in the three-dimensional images, and other parameters are held and updated in the common parameter holding memory 8. The surface-mode image rendering block 5b and volume-mode image rendering block 5a always share the same parameters. Moreover, the image synthesizing unit 6 reads surface-rendering data or volume-rendering data. The read data is output to the monitor 7.

The image synthesizing unit 6 changes the ratio of surface-rendering data to volume-rendering data to allow varying ratios of surface features (by surface-rendering) and depth textures (by volume-rendering) in the resulting image.

To be more specific, when the power supply of the ultrasonic image processing apparatus 1 is turned on, predetermined initialization is carried out. The image synthesizing unit 6 then displays, as indicated at step S1 in FIG. 2, a retrieval dialog box 10 as shown in FIG. 3 on the monitor 7. The retrieval dialog box 10 includes a file retrieval tag 11, a patient information retrieval tag 12, and an examination information retrieval tag 13. The file retrieval tag 11 is used to retrieve an image by a file name. The patient information retrieval tag 12 is used to retrieve an image by patient information such as a patient identification number, a patient name, a date of birth, an examination-time, age, and/or gender. The examination information retrieval tag 13 is used to retrieve an image by examination information such as a date of frozen-image production, a time of frozen-image production, a hospital name, a range of display, a stroke, a pitch, a frequency, a gain, contrast, and/or a level of image quality. An image can thus be retrieved based on various kinds of information.

Figure 2:
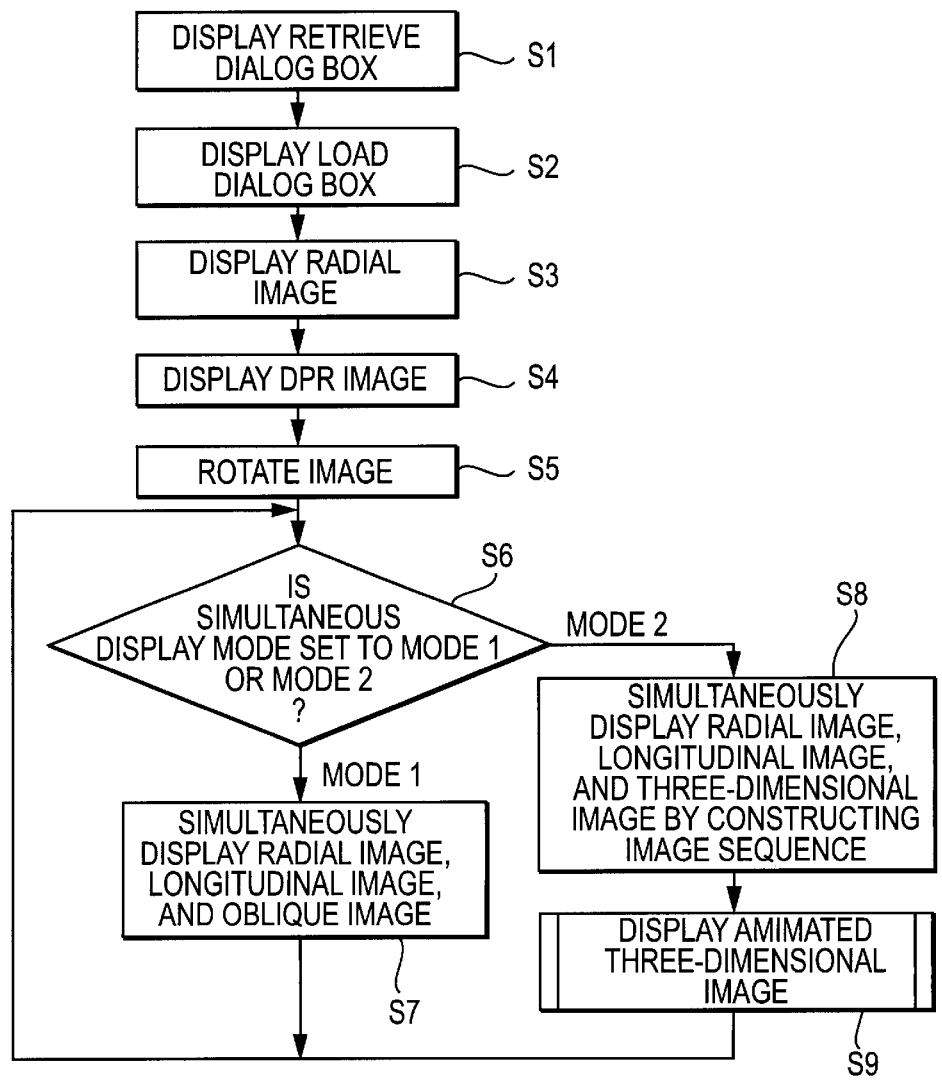
Figure 3:
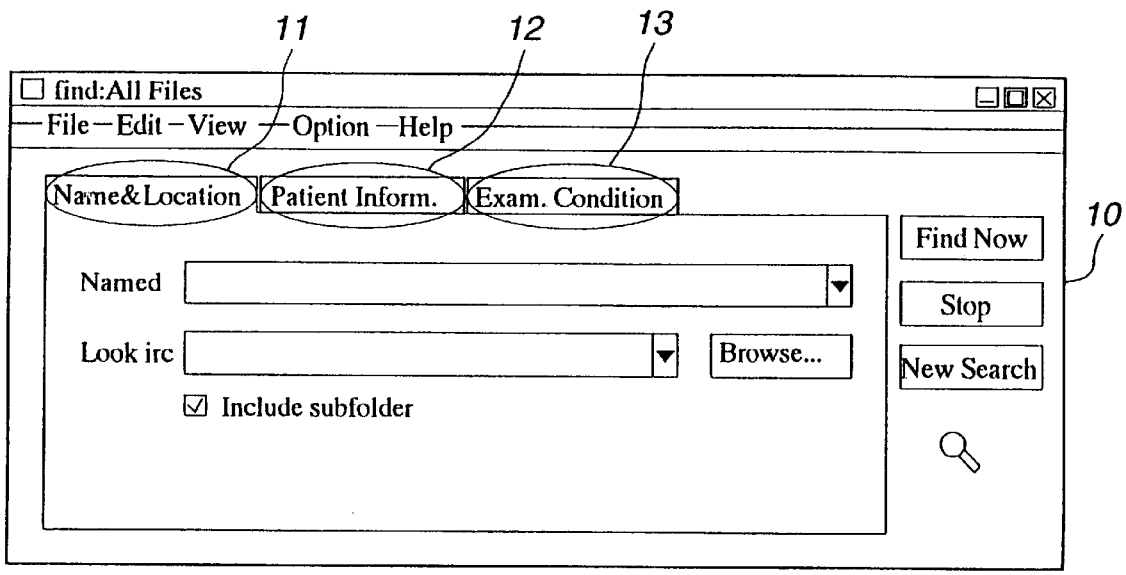
Figure 4:
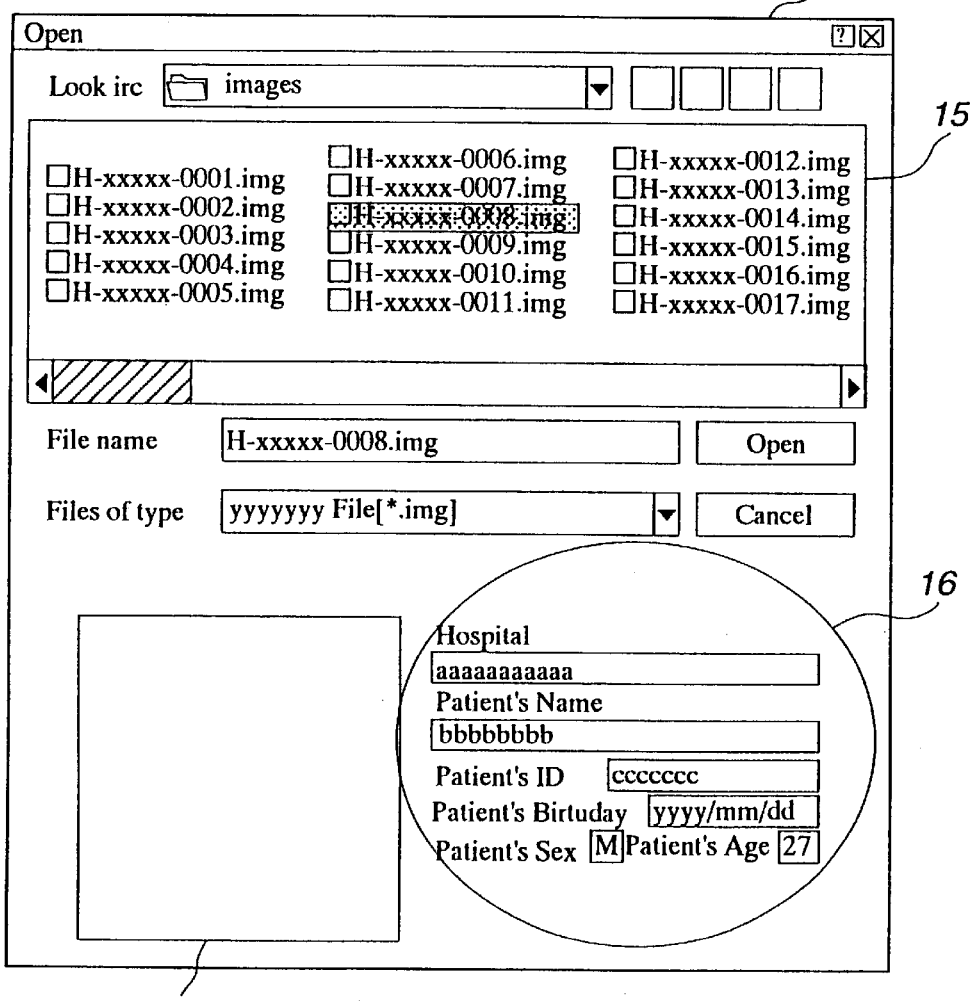

After an image is retrieved using the retrieval dialog box 10, the image synthesizing unit 6 displays a loading dialog box 14 as shown in FIG. 4 on the monitor 7 at step S2 (see FIG. 2). The loading dialog box 14 includes an image file indication area 15, a patient information indication area 16, and a preview image display area 17. A desired data file is selected from among a plurality of three-dimensional image data files indicated in the image file indication area 15. Patient information relevant to the selected data file is displayed in the patient information indication area 16, and a preview image of the selected data file is displayed in the preview image display area 17.

If loading of the desired file is instructed using the loading dialog box 14, loading of the desired file is started at step S3

Figure 5:
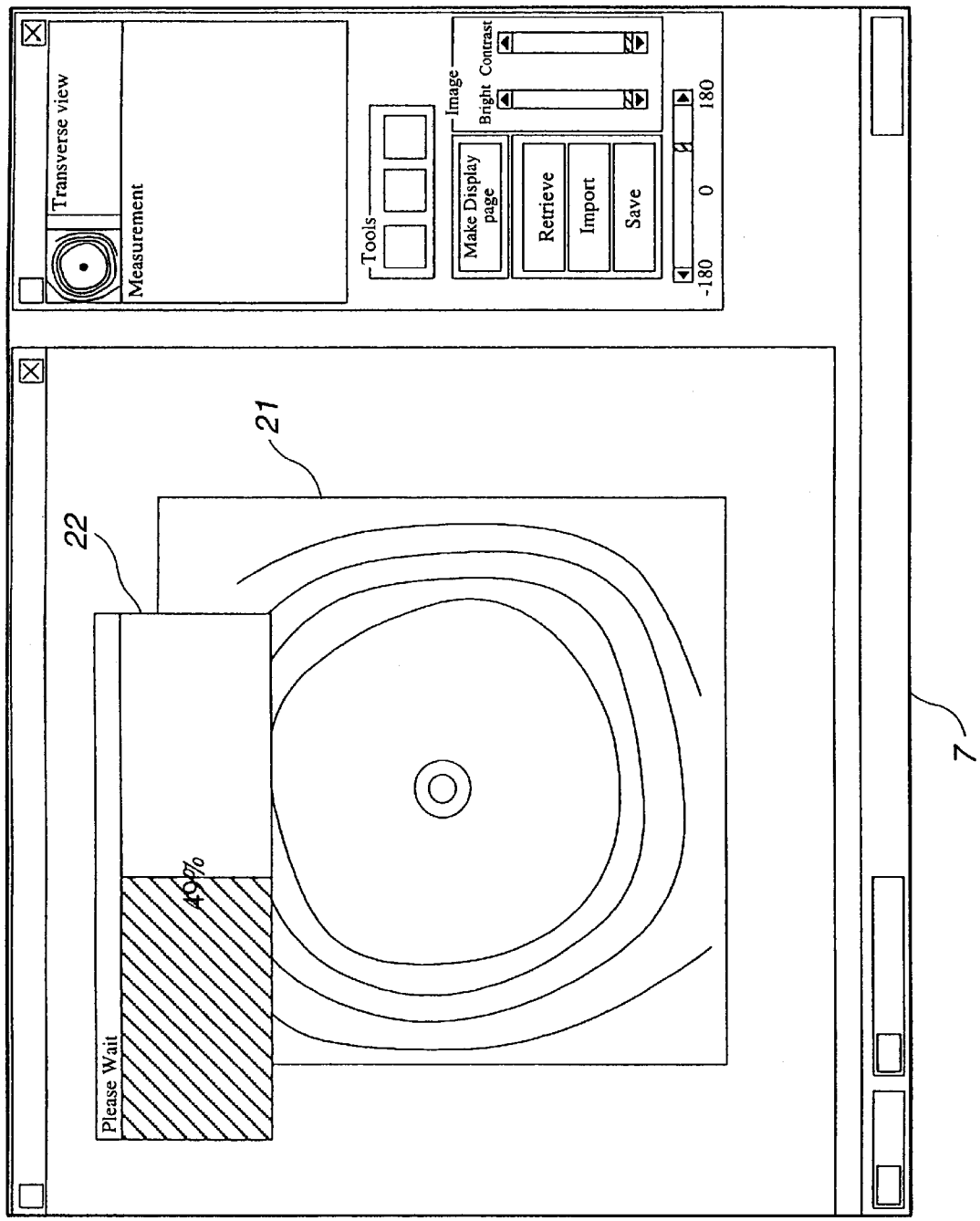

(see FIG. 2). The image synthesizing unit 6 then displays a radial image 21 as shown in FIG. 5 on the monitor 7. While loading is in progress, a progress bar 22 indicating the progress of reading the file appears on the radial image 21.

Figure 6:
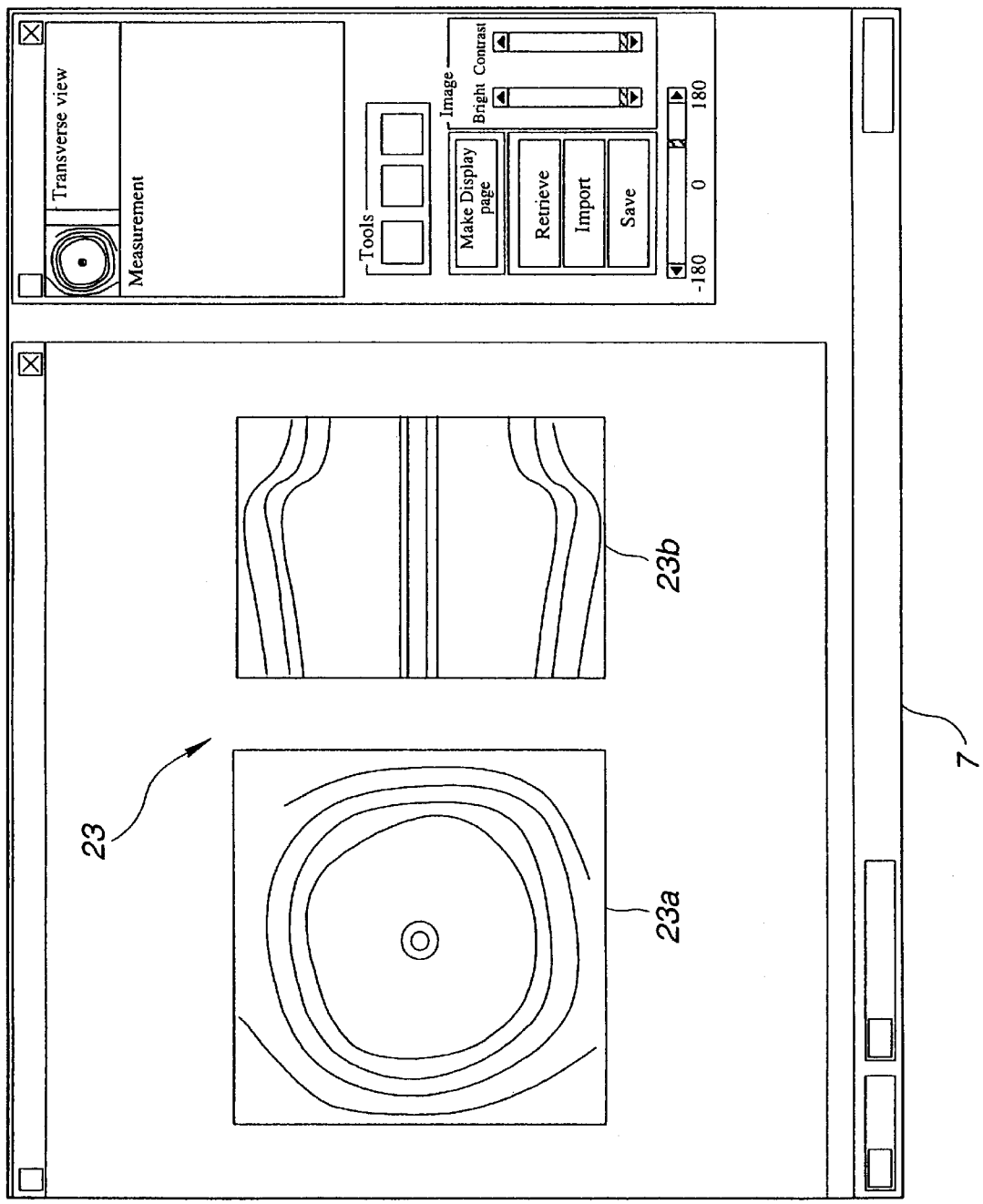

When loading of the data file is completed, the image synthesizing unit 6 displays a dual plane reconstruction (DPR) image 23 on the monitor 7 at step S4 (see FIG. 2), or in other words, concurrently displays a radial image 23a and a linear image 23b as shown in FIG. 6.

Figure 7:
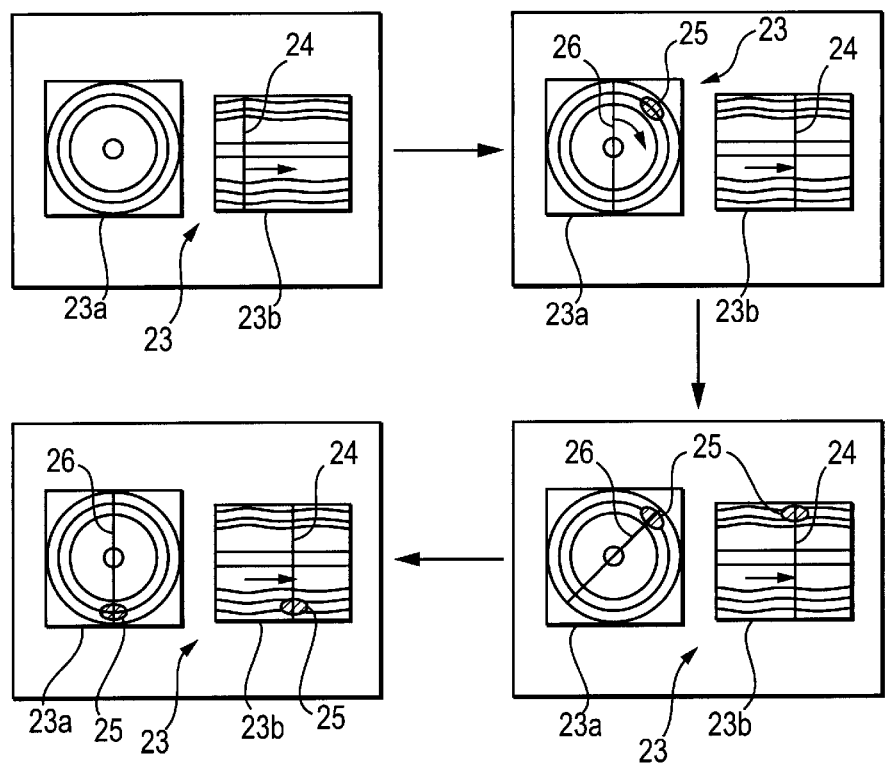

Thereafter, the image synthesizing unit 6 rotates an image at step S5 (see FIG. 2). The image rotation of step S5 will be described more particularly. As shown in FIG. 7, a position setting line 24 appearing in the linear image 23b of the DPR image 23 is moved linearly. As a position designated with the position setting line 24 varies with the movement of the line, the radial image 23a changes correspondingly and continuously. A region of interest 25 is thus located in the radial image 23a. Thereafter, an angle setting line 26 appearing in the radial image 23a is rotated with the radial image 23a as a center until the angle setting line 26 overlays the region of interest 25. Consequently, the region of interest 25 appears on the linear image 23b. Thus, the region of interest 25 is displayed in both the radial image 23a and linear image 23b of the DPR image 23. The radial image 23a and angle setting line 26 may be rotated simultaneously, whereby the region of interest can be moved, for example, to the six o'clock position. The angle setting line may be returned on an initial angle. Additionally, the image rotation may be reflected on an oblique image (see FIG. 10) or a three-dimensional image (see FIG. 11).

Figure 8:
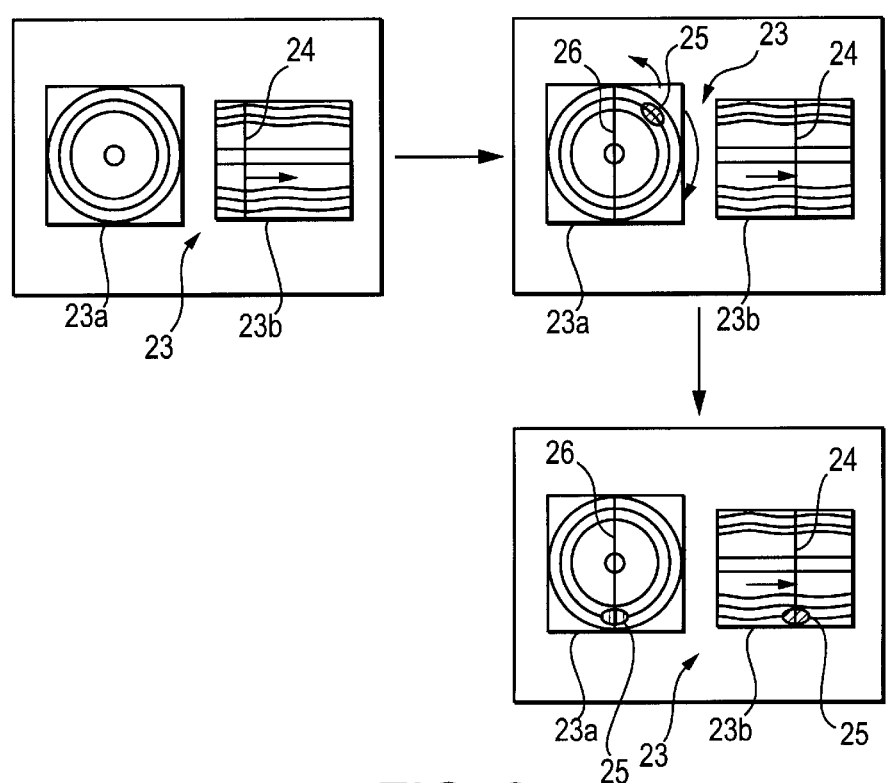

A variation of the image rotation of step S5 will be described below. As shown in FIG. 8, the position setting line 24 appearing on the linear image 23b of the DPR image 23 is moved linearly. As a position designated with the position setting line 24 varies with the movement of the line, the radial image 23a changes correspondingly and continuously. The region of interest 24 is then located in the radial image 23a. Thereafter, the radial image 23a is rotated with the angle setting line 26 immobilized. The angle setting line 26 is thus overlaid on the region of interest 25. Subsequently, the region of interest 25 is also displayed in the linear image 23b.

Figure 9:
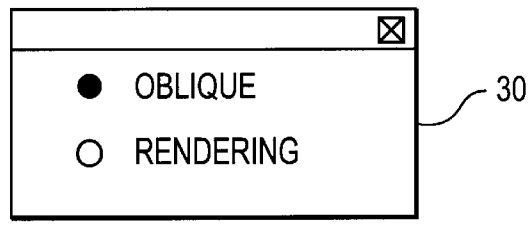

When the processing of step S5 is completed, a mode selection dialog box 30 as shown in FIG. 9 is used to select either the first concurrent display mode or the second concurrent display mode at step S6. In the first concurrent display mode, a radial image (X-Y view), longitudinal images (Y-Z vie and X-Z view), and an oblique image rendering sections using texture data are displayed concurrently. In the second concurrent display mode, the radial image (X-Y view), the longitudinal image (Y-Z view and X-Z view), and a three-dimensional image rendering sections using texture data and an intracavitary wall using surface-rendering data are displayed concurrently. The surface-rendering data used to construct the three-dimensional image may be replaced with a combination of the surface-rendering data and volume-rendering data.

Figure 10:
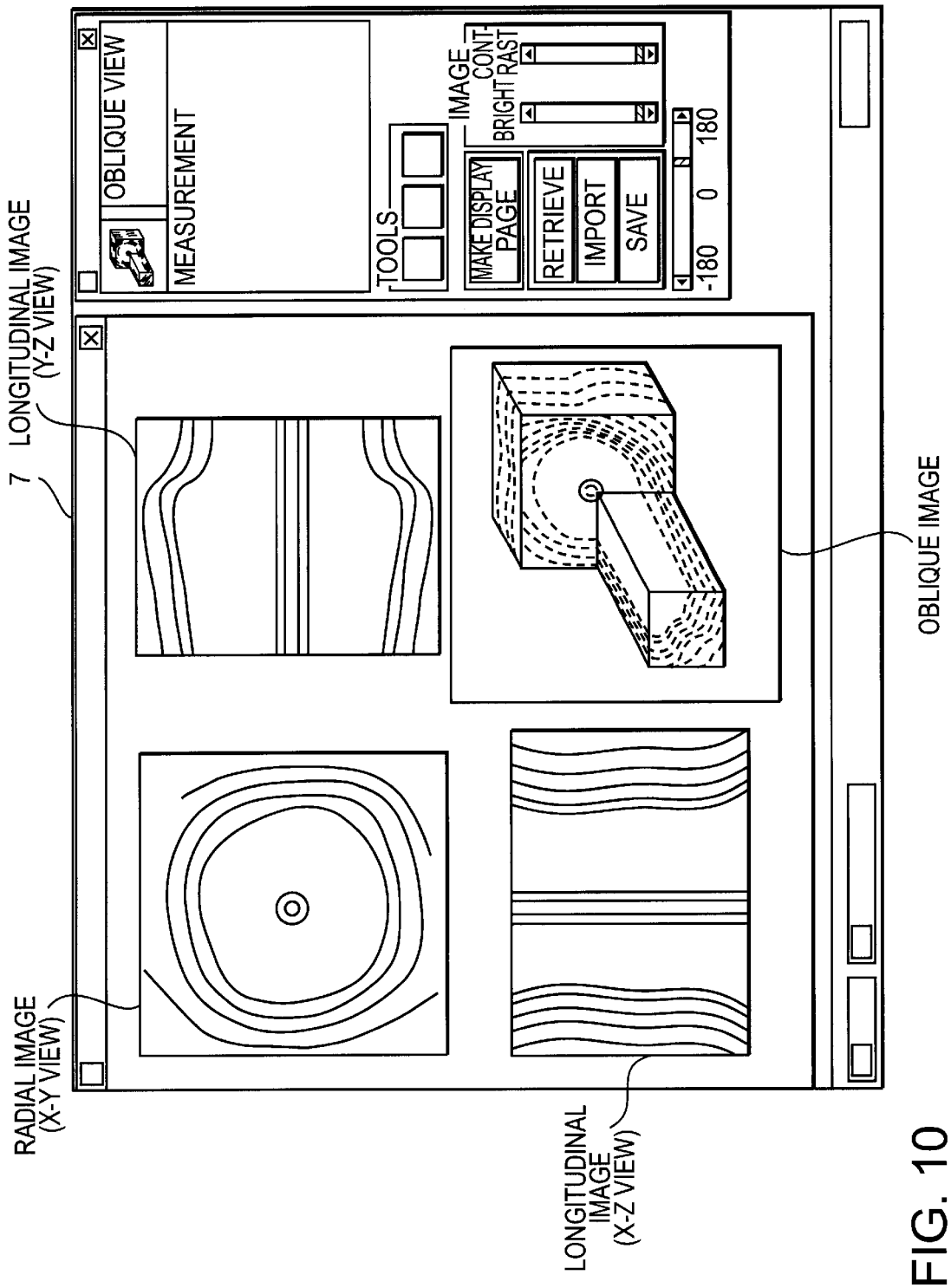

If "Oblique" is selected in the mode selection dialog box 30, it means that the first mode has been designated. The image synthesizing unit 6 therefore displays, as shown in FIG. 10, a radial image (X-Y view), longitudinal images (Y-Z view and X-Z view), and an oblique image, which renders sections using texture data, on the monitor 7. Control is then returned to step S6, and the process is repeated.

Figure 11:
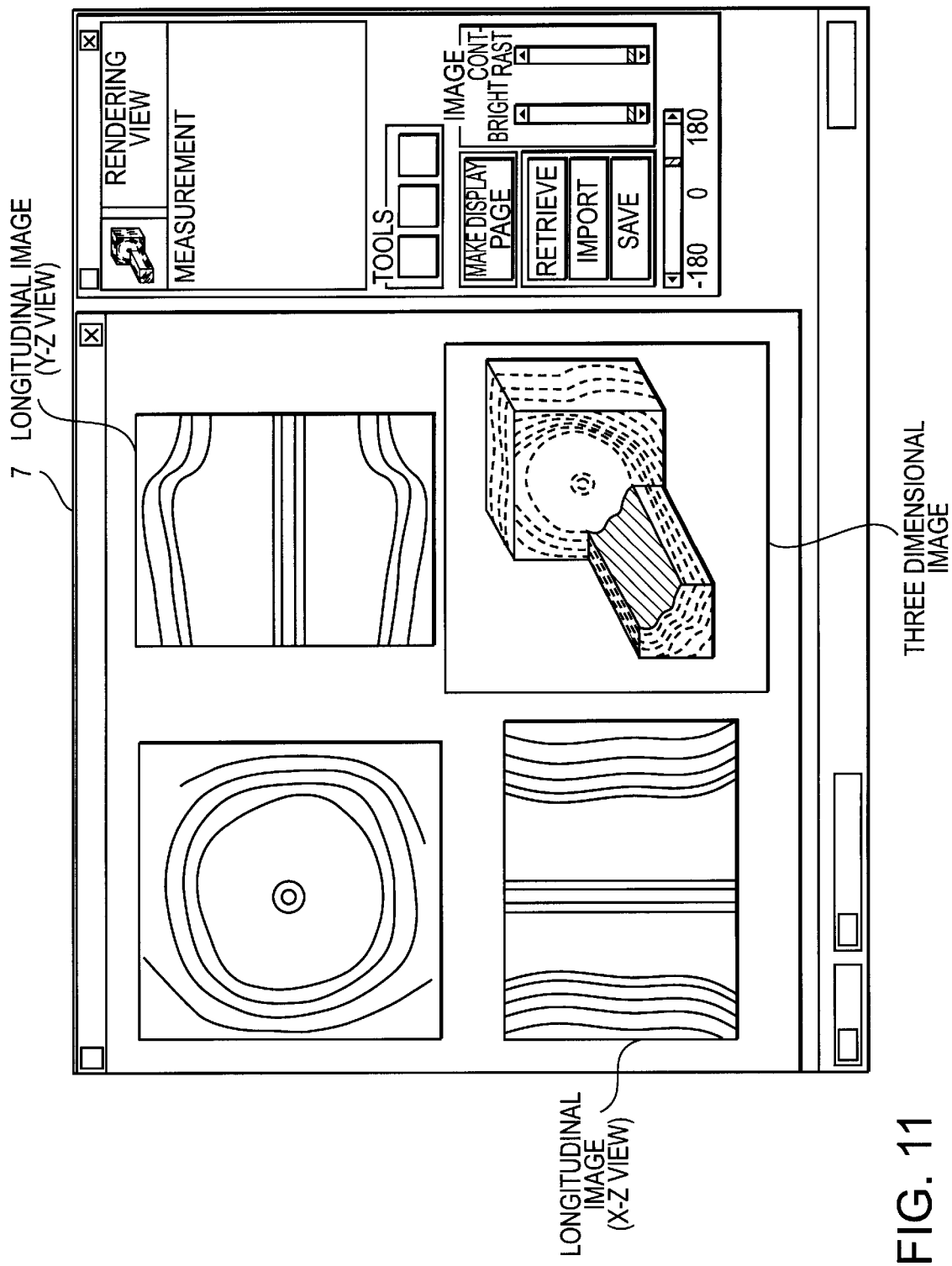

If "Rendering" is selected in the mode selection dialog box 30, it means that the second mode has been designated. The image synthesizing unit 6 therefore displays, as shown in FIG. 11, a radial image (X-Y view), longitudinal images (Y-Z view and X-Z view), and a three-dimensional image, which renders sections using texture data and an intracavitary wall using surface-rendering data, on the monitor 7. The surface-rendering data used to construct the three-dimensional image may be replaced with a combination of the surface-rendering data and volume-rendering data. At step S9, the three-dimensional image is animated. Control is then returned to step S6, and the process is repeated.

Animation of a three-dimensional image at step S9 is such that the three-dimensional image is rotated continuously a plurality of times and then read and displayed time-sequentially. A plurality of three-dimensional images rendering the rotated image at different angles is obtained as will be discussed later and stored in the memory in the three-dimensional image (stacked data) rendering unit 5.

Figure 12:
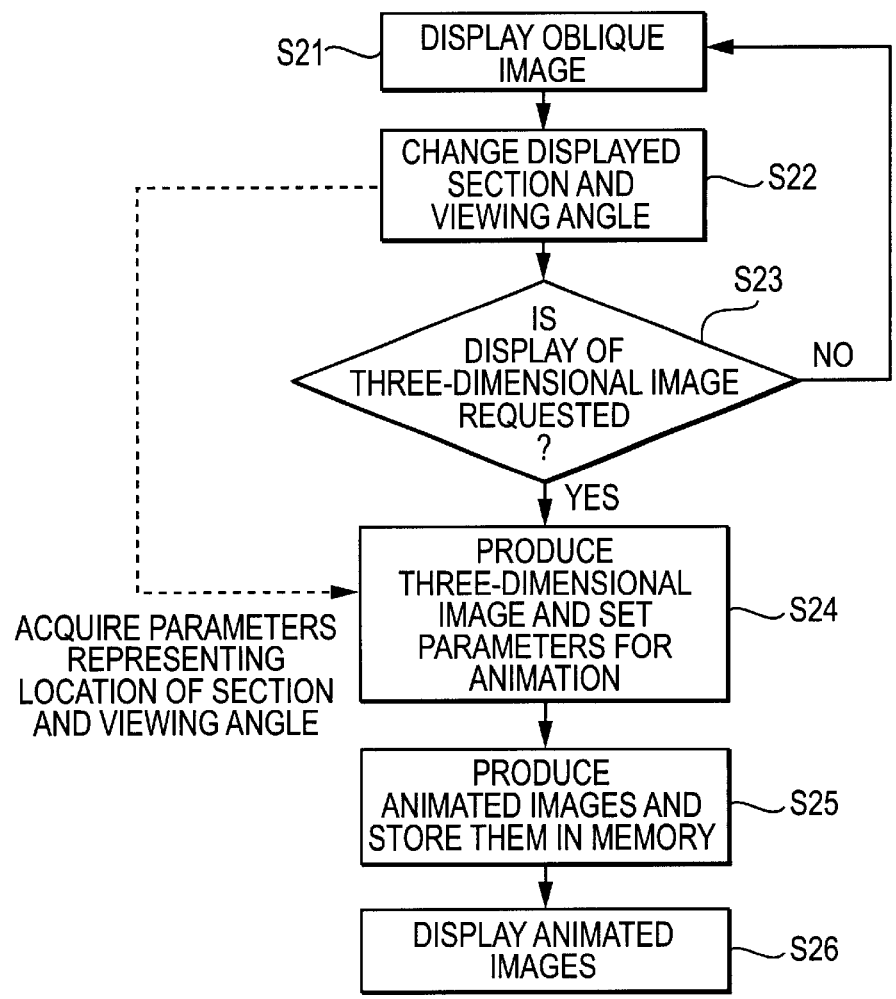

Specifically, as indicated in FIG. 12, an oblique image produced by the oblique image rendering unit 3 is displayed at step S21. The positions of the sections rendered in the oblique image and the viewing angle of the oblique image are changed at step S22. A request for display of a three-dimensional image is awaited at step S23. On a request for display of a three-dimensional image, a three-dimensional image is produced at step S24. Parameters of an animated image are set based on the positions of the sections rendered in the oblique image and the viewing angle of the oblique image changed at step S22. At step S25, based on the parameters of an animated image, an animated image is produced using a plurality of three-dimensional images produced by continuously shifting the viewing angle and stored in the memory in the three-dimensional image rendering unit 5. The animated image is read and displayed time-sequentially at step S26.

Thereafter, a description will be made of an oblique image, which is shown in FIG. 10, rendering sections using texture data, and of a three-dimensional image, which is shown in FIG. 11, rendering sections using texture data and an intracavitary wall using surface-rendering data.

Figure 13:
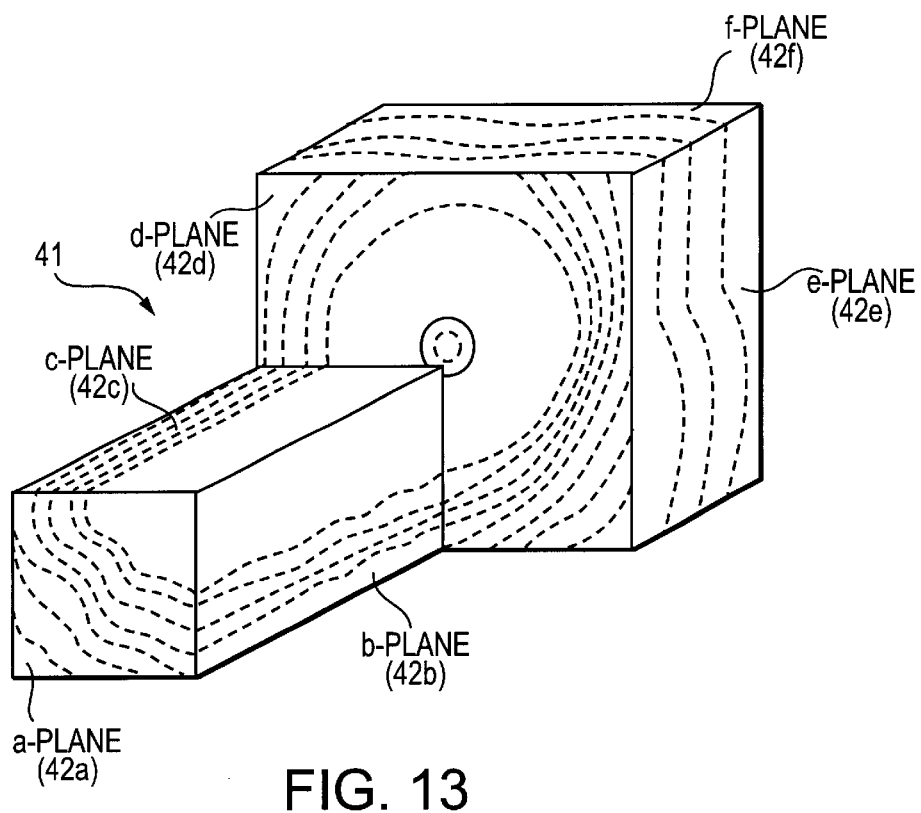

As shown in FIG. 13, an oblique image 41 rendering sections using texture data is produced by the oblique image rendering unit 3. The oblique image 41 is produced by appending texture data 42 to section data (plans a, b, c, d, e, and f) of an oblique image produced by the oblique image rendering unit 3. The texture data 42 represents the layered structure of an intracavitary tissue according to data produced by the volume-mode image rendering block 5a.

Figure 14:
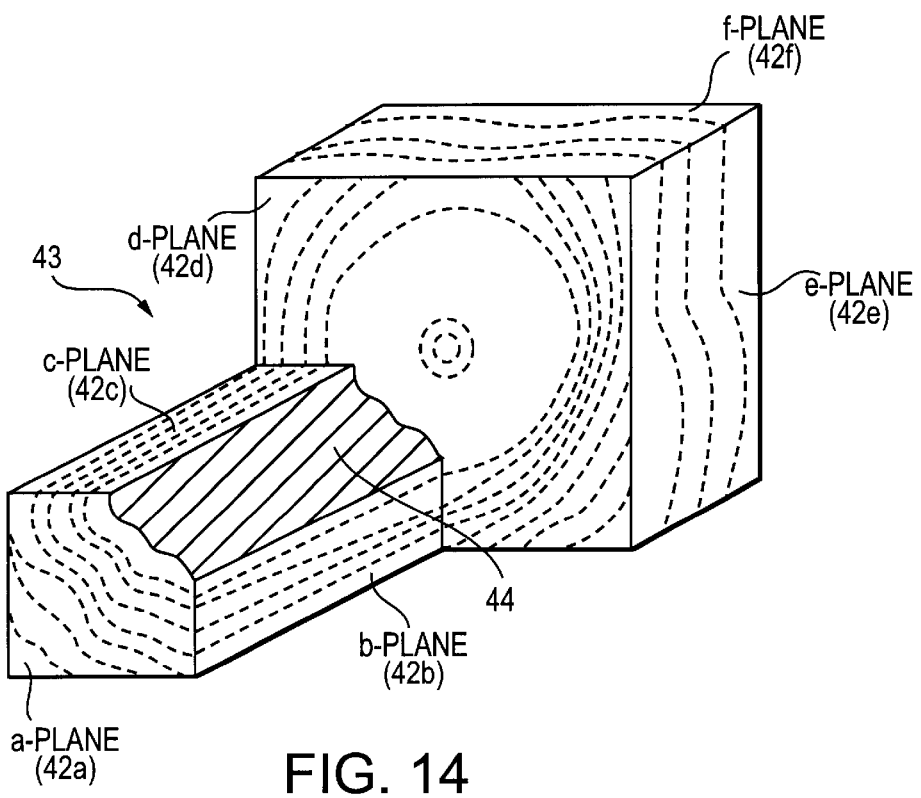

As shown in FIG. 14, a three-dimensional image 43 rendering sections using texture data and an intracavitary wall using surface-rendering data is produced by appending texture data 42 to section data (planes a, b, c, d, e, and f) of an oblique image produced by the oblique image rendering unit 3. The texture data 42 represents the layered structure of an intracavitary tissue according to data produced by the volume-mode image rendering block 5a. Moreover, the image data of an intracavitary wall is extracted and surface-rendering data 44 is appended to the extracted data of the intracavitary wall.

Figure 15:
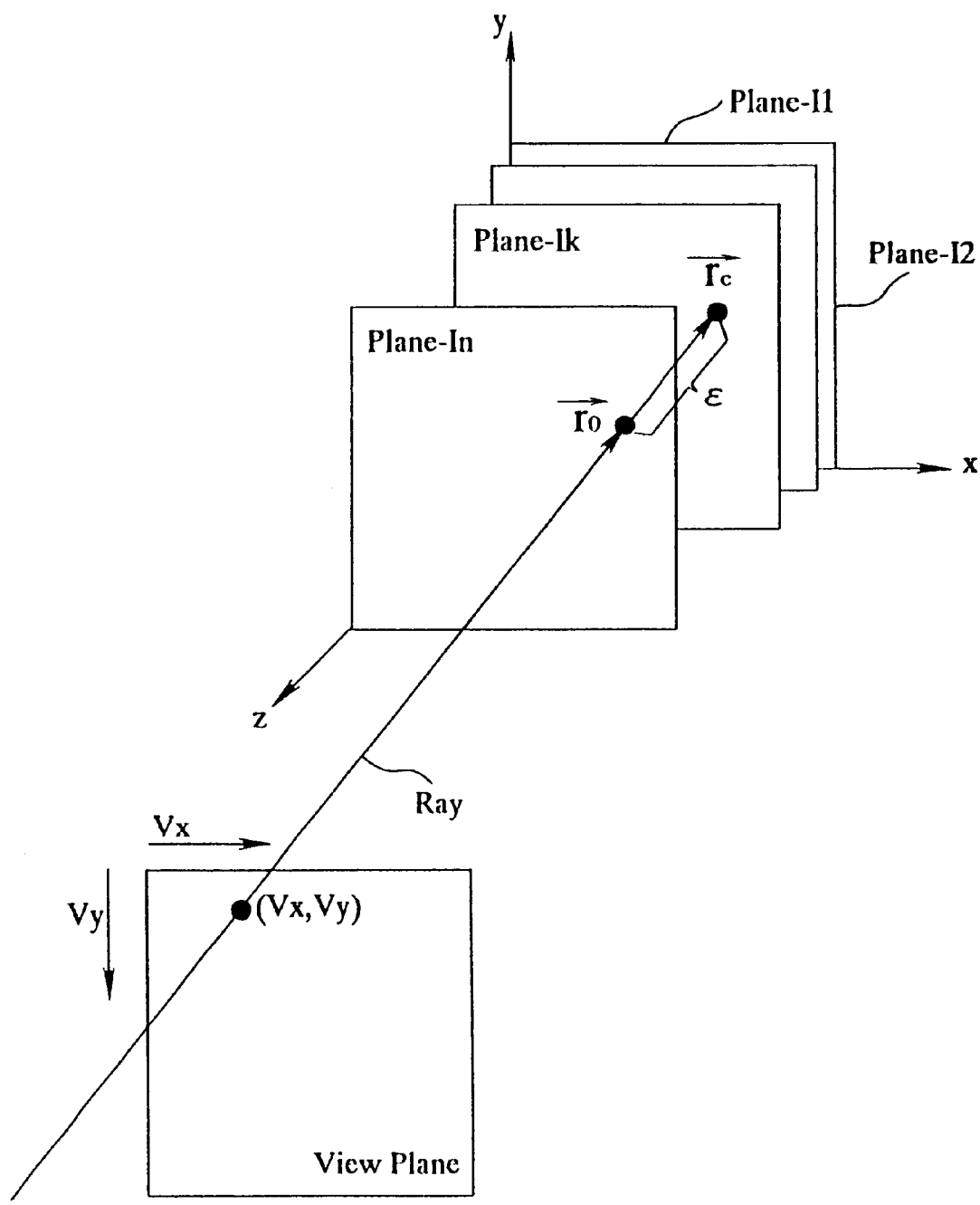
Figure 16:
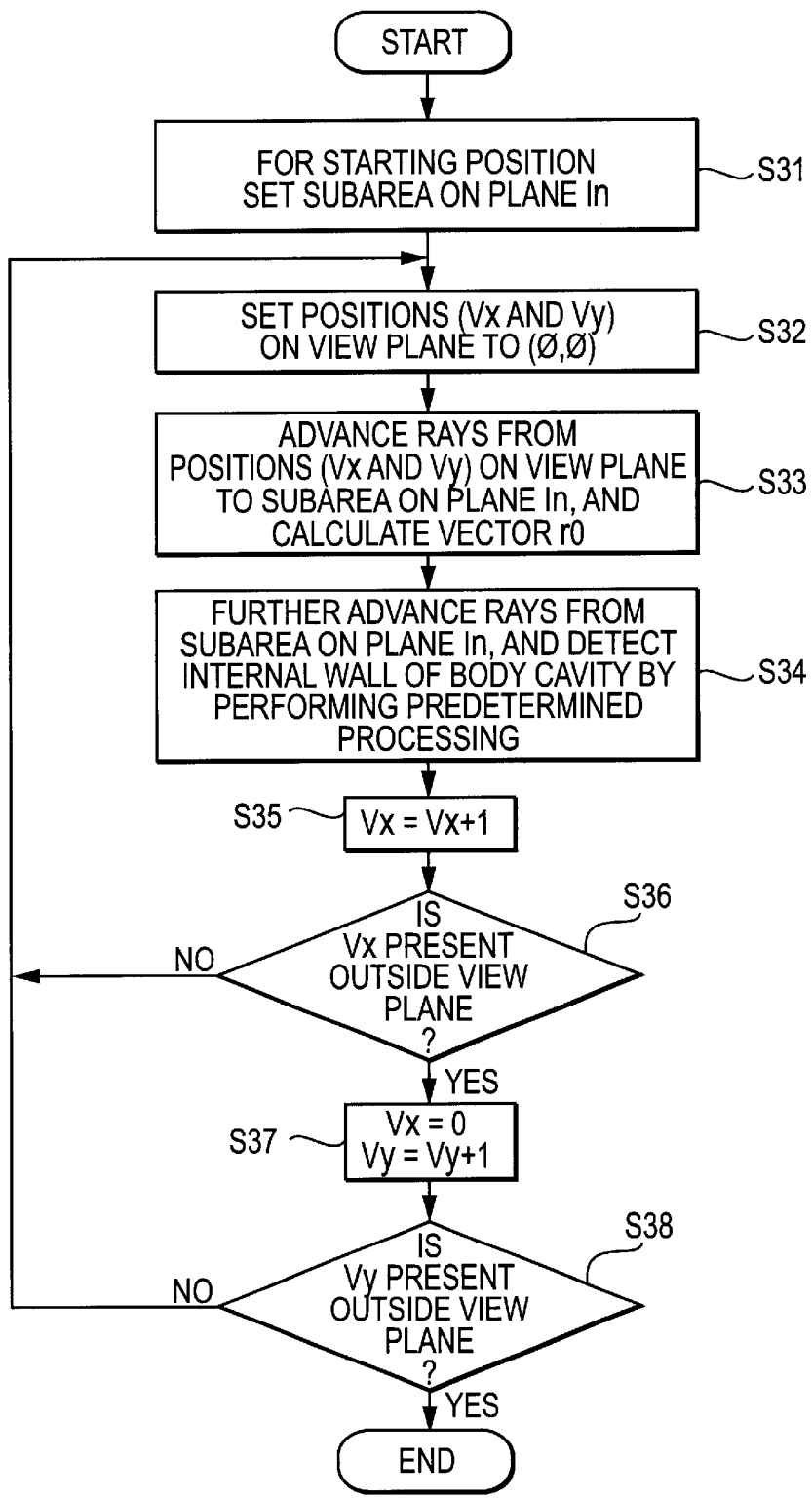

Extracting the image data of an intracavitary wall will be described below. First, as shown in FIG. 15, an area of a three-dimensional image (stacked data) which is limited by an oblique image is divided into a plurality of layered planes I1, I2, etc., and In. As indicated at step S31 in FIG. 16, a small area is defined on the plane In. A position (Vx, Vy) on a view plane is set to (0,0) at step S32. At step S33, a ray is advanced from the position (Vx, Vy) on the view plane to the small area on the plane In, and a vector r0 is defined (see FIG. 15). Herein, the ray is a virtual ray defining a straight line that extends from an observer's eye located at an infinite distance. Rays passing through positions on the view plane are therefore parallel rays.

Thereafter, the ray is further advanced from the small area on the plane In, and a predetermined process to be described later is carried out in order to detect data of an intracavitary wall.

At step S35, the position (Vx, Vy) is set to (Vx+1, Vy). It is judged at step S36 whether (Vx+1, VY) lies outside the view plane. If (Vx+1, Vy) lies within the view plane, control is returned to step S33 and the process is repeated. If (Vx+1, Vy) lies outside the view plane, the position (Vx, Vy) is set to (0, Vy+1) at step S37. It is judged at step S38 whether (0, Vy+1) lies outside the view plane. If (0, Vy+1) lies within the view plane, control is returned to step S33 and the process is repeated. If (0, Vy+1) lies outside the view plane, the process is terminated. Consequently, the oblique image is scanned with the ray advanced from all positions on the view plane.

The predetermined process of step S34 will be described below. The vector r0 is, as mentioned above, defined along the ray advanced from the position (Vx, Vy) on the view plane to the small area on the plane In.

The ray is thus advanced from the position (Vx, Vy) on the view plane to the small area on the plane In and further advanced from the small area on the plane In to a plane In−1 of the next layer. A vector extending from the position (Vx, Vy) to the small area on the plane In−1 is defined as a vector rc (see FIG. 15). In other words, the vector rc starts at the initial point of the vector r0 (position (Vx, Vy)) and ends at a point in a small area on a plane I1. The length of the vector rc therefore sequentially increases up to the length to the plane I1.

Figure 17:
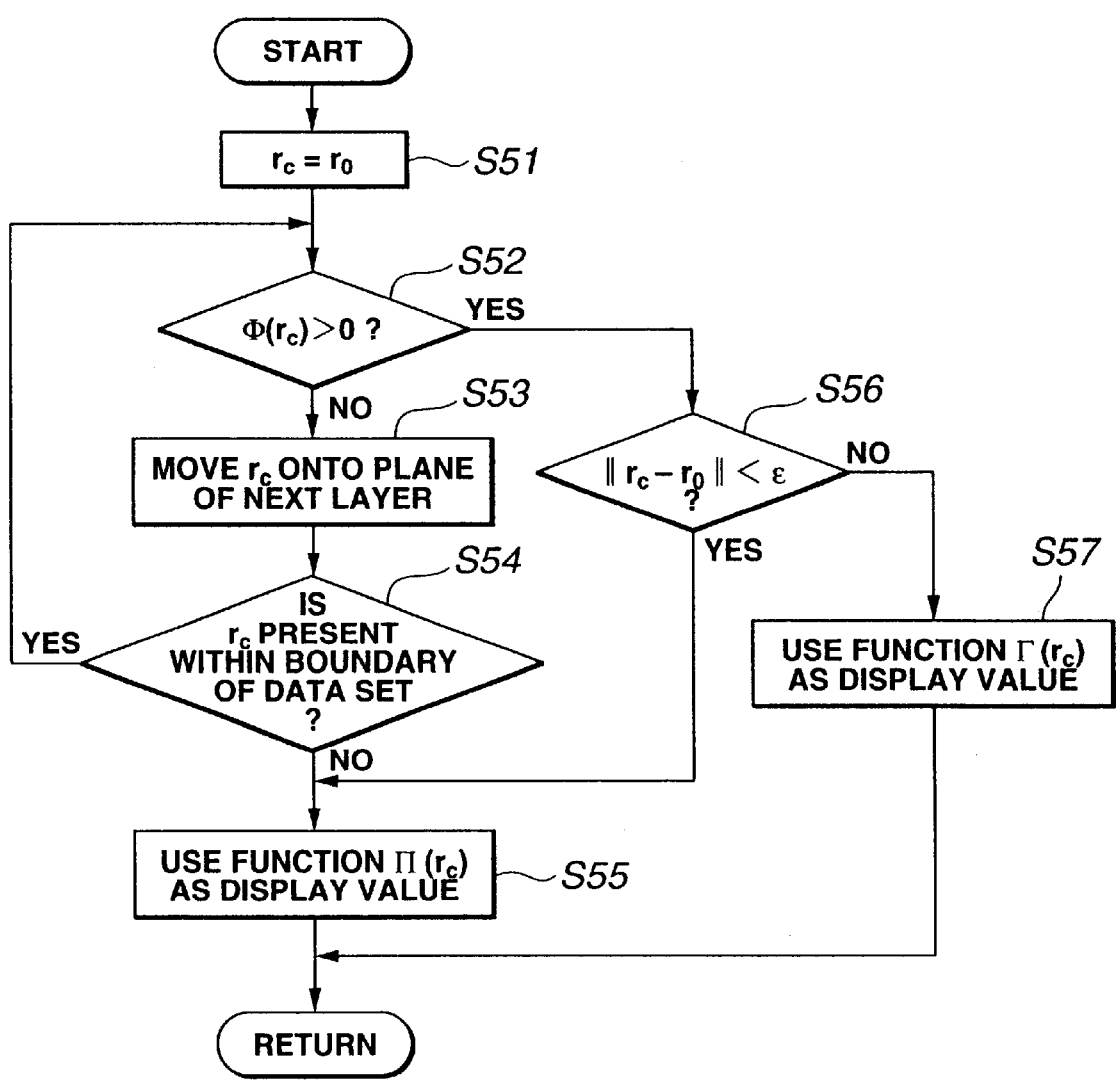

In the predetermined process of step S34, the vectors r0 and rc are used. As described in FIG. 17, the point rc is set to r0. At step S52, a function Φ (rc) is solved with rc set to r0. It is then judged whether Φ (rc) returns to a value larger than 0. The function Φ (rc) serves to judge whether the result of an arithmetic operation performed on data values of points on layers which adjoin the point rc is a value of 0 or 1. The function is thus used to judge whether data of the point rc contributes to the rendering of a three-dimensional image. At step S52, if Φ (rc) returns a value of 0, it is judged that the data of the point rc does not contribute to the rendering of a three-dimensional image. If Φ (rc) returns a value of 1, (>0), it is judged that the data of the point rc contributes to the rendering of a three-dimensional image. For example, when the result of an arithmetic operation performed on data values of ten points on the ray adjoining the point rc falls below a predetermined threshold, Φ (rc) is determined to be 0.

If Φ (rc) is determined to be 0, it is judged that the data of the point rc does not contribute to the rendering of a three-dimensional image. At step S53, the point rc is shifted to a point on a plane Ik of the next layer. It is judged at step S54 whether the data of the new point rc is a boundary value of the data set consisting of data values concerning points on a plurality of planes I1, I2, etc., and In. If the data of the point rc is a boundary value of the data set, control is returned to step S52 and the process is repeated. If the data of the point rc is not a boundary value, a function II (rc) is adopted as a representational value used to construct a three-dimensional image. The process is then terminated.

The function II (rc) provides volume-rendering data.

At step S52, if Φ (rc) yields a value of 1 (>0), it is judged that the data contributes to the rendering of a three-dimensional image. It is judged at step S56 if the difference between the length of the vector r0 and that of the vector rc ||r0-rc||, falls below a predetermined value ε. If the difference ||r0-rc|| falls below the predetermined value ε, control is passed to step S55. If the difference ||r0-rc|| is equal to or larger than the predetermined value ε, a function Γ (rc) is adopted as a representational value used to construct a three-dimensional image. The process is then terminated.

The function Γ (rc) provides surface-rendering data. For example, the function Γ (rc) provides data concerning shade covering six points in space proximate to point rc and caused by illumination.

Owing to the foregoing process, a three-dimensional image can be produced by appending surface-rendering data and volume-rendering data to data of an intracavitary wall. This leads to drastically improved diagnosis. Moreover, for extracting the data of an intracavitary wall, the function Φ (rc) is used and the difference ||r0-rc|| between the length of the vector r0 and the length of the vector rc is judged. The three-dimensional image can therefore be constructed quickly.

The thus constructed three-dimensional image 43 includes, as shown in FIG. 14, surface-rendering data 44 rendering the surface of an intracavitary wall and volume-rendering data providing the internal information of the intracavitary wall. The sections of the intracavitary wall are rendered using the texture data 42.

Figure 18:
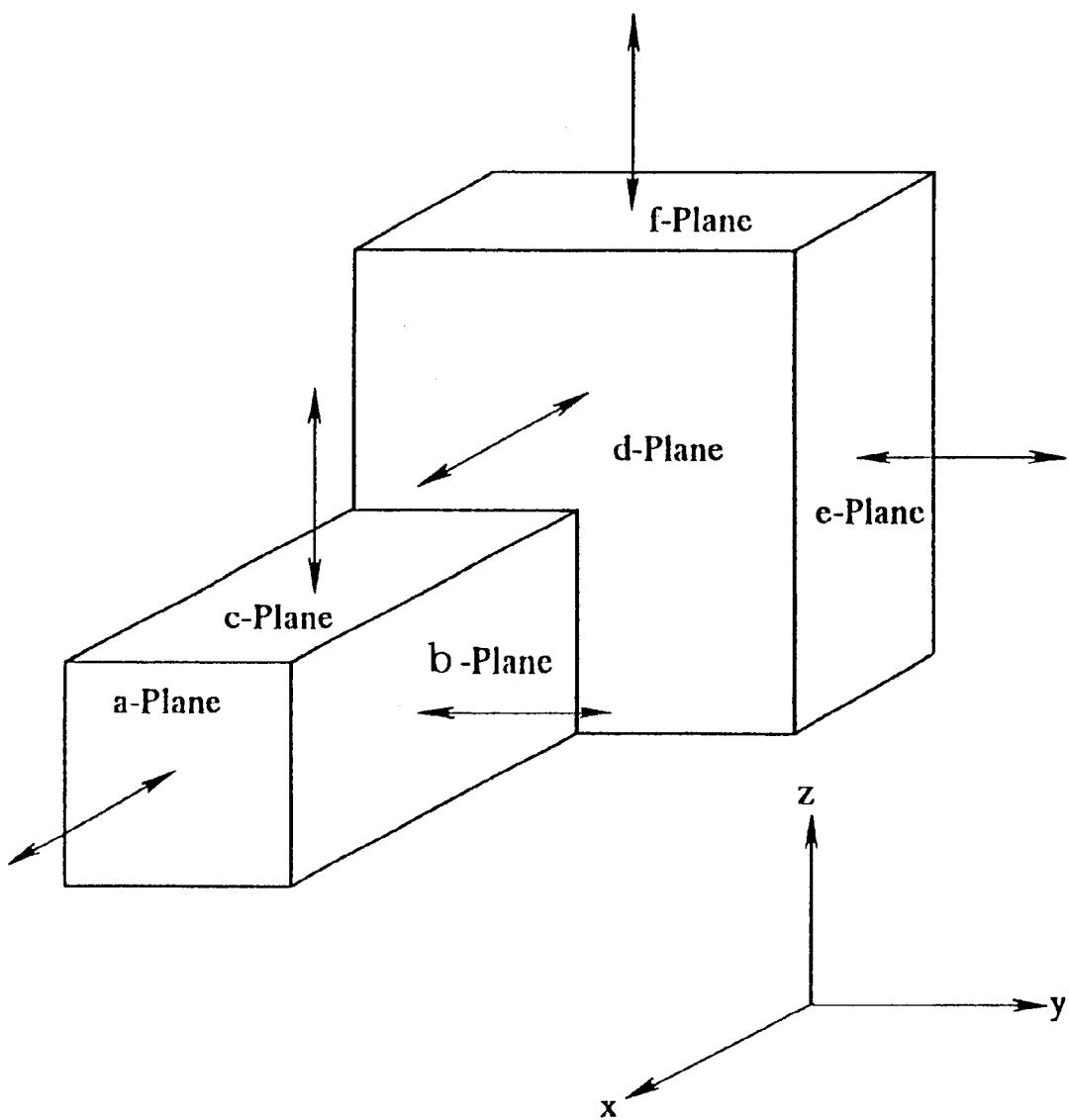
Figure 19:
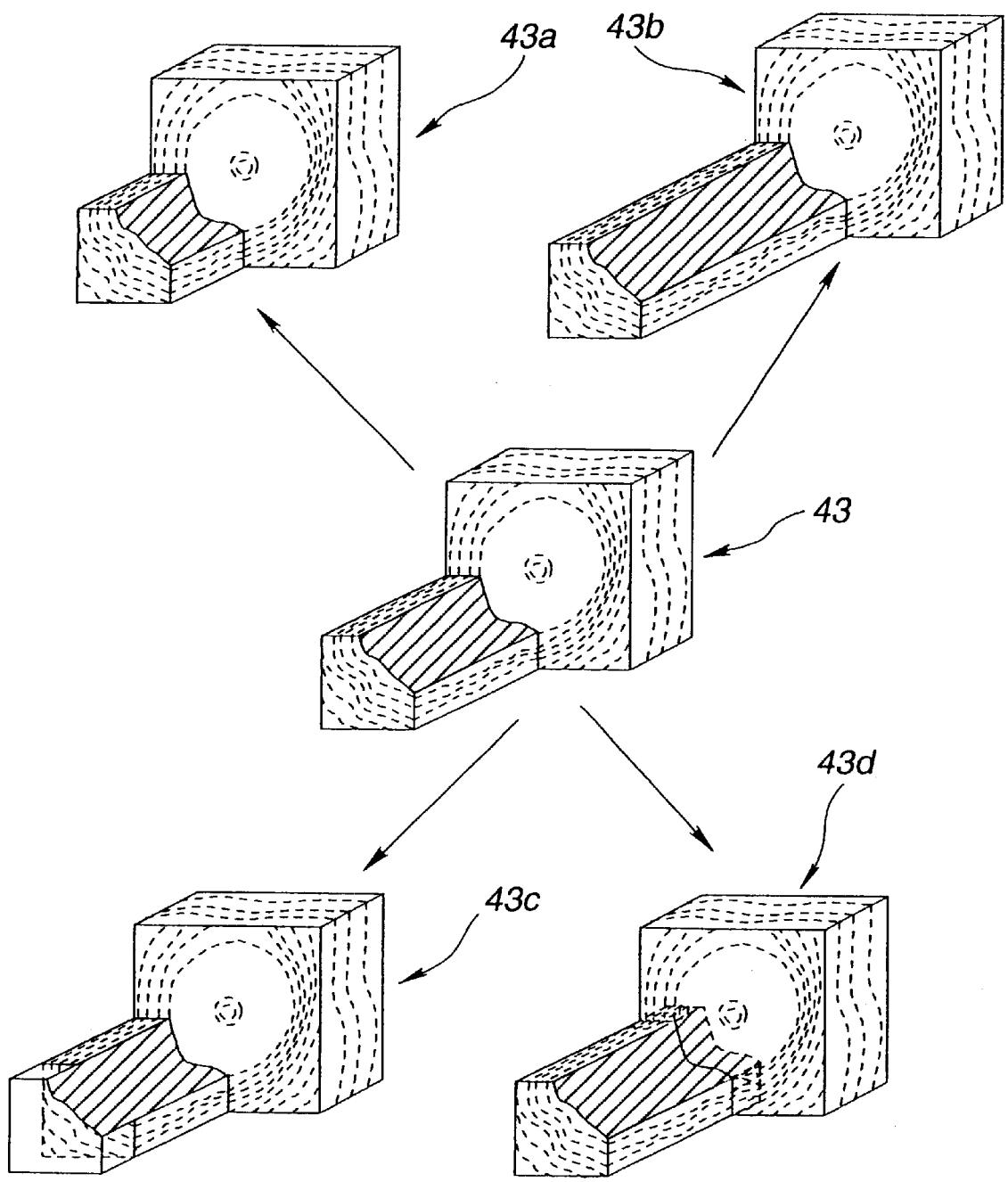

As shown in FIG. 18, sections rendered in the three-dimensional image 43 (planes a, b, c, d, e, and f) can be advanced or withdrawn in the directions of the arrows. A description will be made with respect to plane a as an example. As shown in FIG. 19, a pointing device such as a mouse (not shown) is used to shrink the convex part of the initial three-dimensional image and to subsequently convert the initial three-dimensional image 43 into a three-dimensional image 43a. The convex part is composed of the surface rendering data 44, texture data 42, and volume-rendering data providing internal information of the intracavitary wall.

Moreover, the convex part of the initial three-dimensional image 43 may be stretched to construct a three-dimensional image 43b. Here again, the convex part is composed of the surface-rendering data 44, texture data 42, and volume-rendering data providing internal information of the intracavitary wall.

Furthermore, the initial three-dimensional image 43 may be converted into a three-dimensional image 43c. The convex part of the three-dimensional image 43c includes the surface-rendering data 44 as is but shrinks the texture data 42. The three-dimensional image 43c also includes volume-rendering data providing the internal information of the intracavitary wall.

Furthermore, the initial three-dimensional image 43 may be converted into a three-dimensional image 43d that includes the texture data 42 and volume-rendering data providing the internal information as is. The three-dimensional image 43d has the surface-rendering data 44 extended to a deeper position than in the other images.

(Advantages)

The present embodiment has the advantage of a volume rendering mode of providing internal cavity information, and the advantage of a surface rendering mode of visualizing information of minute irregularities on a surface. Moreover, the present embodiment has the advantage that the resolution of section data is improved due to the appending of the texture data 42.

Moreover, the planes of a three-dimensional image can be freely modified to thus produce the three-dimensional image 43a or 34b. Like the three-dimensional image 43c, while the surface-rendering data 44 may be left intact in order to render the surface of an intracavity wall, internal information thereof can be visualized using the volume-rendering data. Like the three-dimensional image 43d, while the volume-rendering data is left intact in order to render the internal state of an intracavitary wall, information of minute irregularities on the surface of the intracavitary wall can be visualized using the surface-rendering data 44.

Second Embodiment:

(Constituent Features)

The second embodiment is substantially identical to the first embodiment. As such, only the difference will be described. The same reference numerals will be assigned to identical components, and the description of these components will be omitted.

Figure 20:
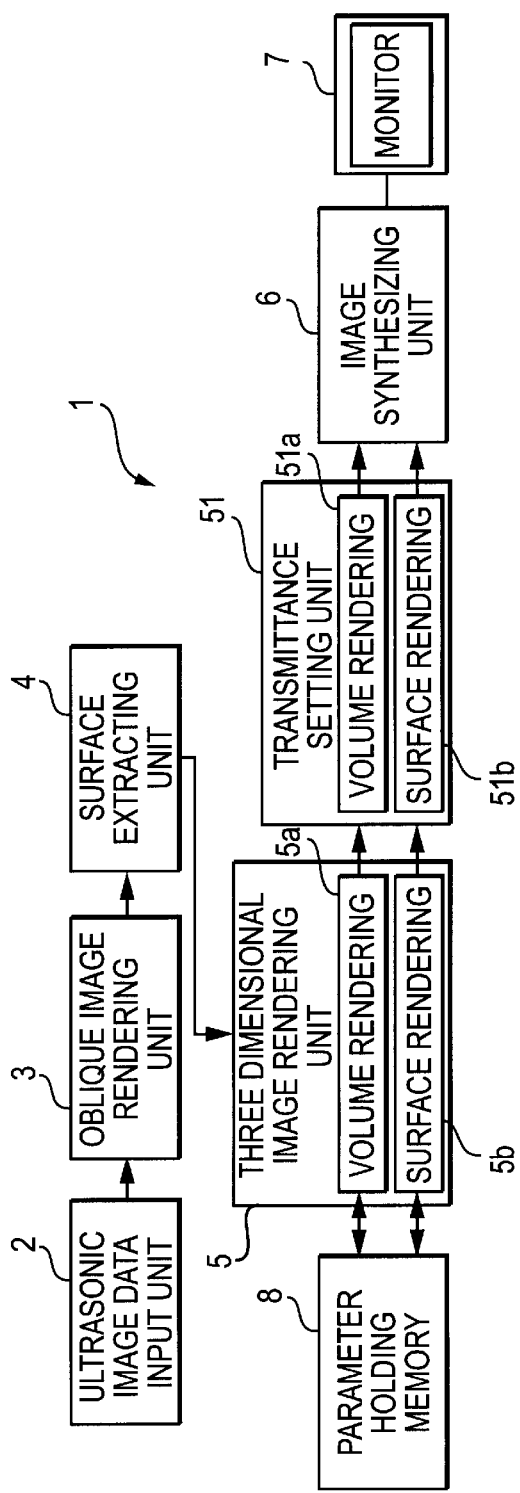
FIGS. 20 to FIG. 22 relate to the second preferred embodiment.

As shown in FIG. 20, according to the present embodiment, a transmittance setting unit 51 composed of a volume-mode transmittance setting block 51a and surface-mode transmittance setting block 51b is interposed between the three-dimensional image rendering unit 5 and image synthesizing unit 6. The volume-mode transmittance setting block 51a sets a transmittance for a volume rendering mode. The surface-mode transmittance setting block 51b sets a transmittance for a surface rendering mode. The transmittance setting unit 51 can thus set the transmittance separately for the volume rendering mode and the surface rendering mode. The other components are identical to those of the first embodiment.

(Operation)

According to the present embodiment, the volume-mode transmittance setting block 51a of the transmittance setting unit 51 sets a transmittance for a volume rendering mode. The surface-mode transmittance setting block 51b sets a transmittance for a surface rendering mode. The image synthesizing unit 6 reads surface-rendering data or volume-rendering data. The read data is output to the monitor 7.

Figure 21:
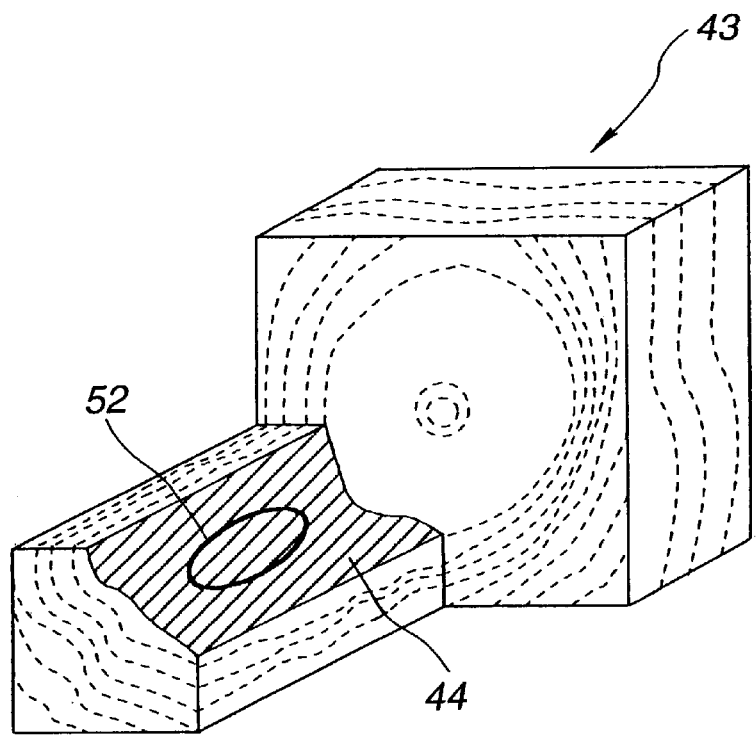

Displayed on the monitor 7 is, as shown in FIG. 21, an image rendering the surface of an intracavitary wall using surface-rendering data, the internal information thereof using volume-rendering data, and the sections thereof using texture data. Transmittance is set separately for the surface rendering mode and the volume rendering mode. Consequently, a region of interest 52 rendered with the volume-rendering data can be discerned externally.

Figure 22:
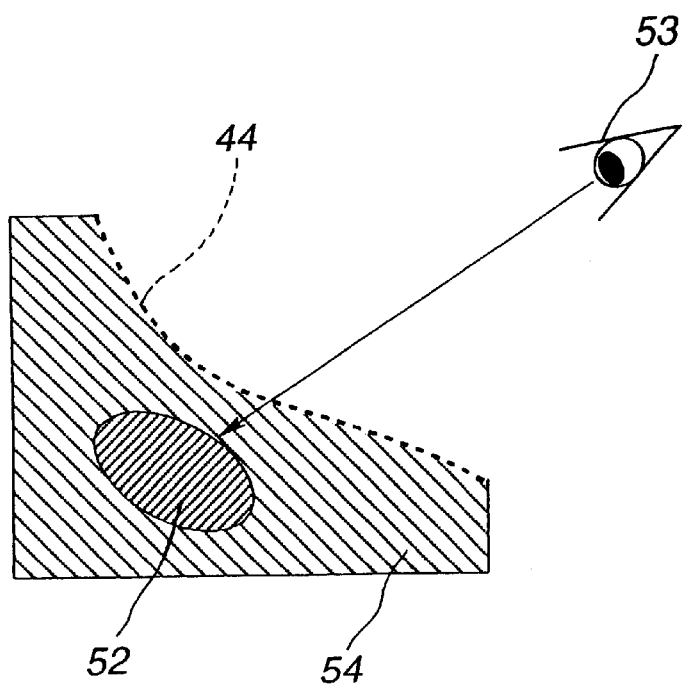

FIG. 22 is a side view of the above image shown in FIG. 21. The region of interest 52 rendered with the volume-rendering data 54 can be discerned externally with an observer's eye 53. However, transmittance must be set separately for producing the surface-rendering data 44 and for producing the volume-rendering data 54.

(Advantage)

The present embodiment can provide the same advantages as the first embodiment. In addition, information of minute irregularities on the surface of an intracavitary wall can be observed using the surface-rendering data 44. At the same time, the volume-rendering data 54 provides the internal information of the intracavitary wall. Since a transmittance for producing the surface-rendering data 44 and a transmittance for producing the volume-rendering data 54 can be set mutually independently, the region of interest 52 rendered in the three-dimensional image can be observed concurrently with the surface of the intracavitary wall.

Third Embodiment:

(Constituent Features)

The third embodiment is substantially identical to the first embodiment. As such, only the difference will be described. The same reference numerals will be assigned to identical components, and the description of these components will be omitted.

Figure 23:
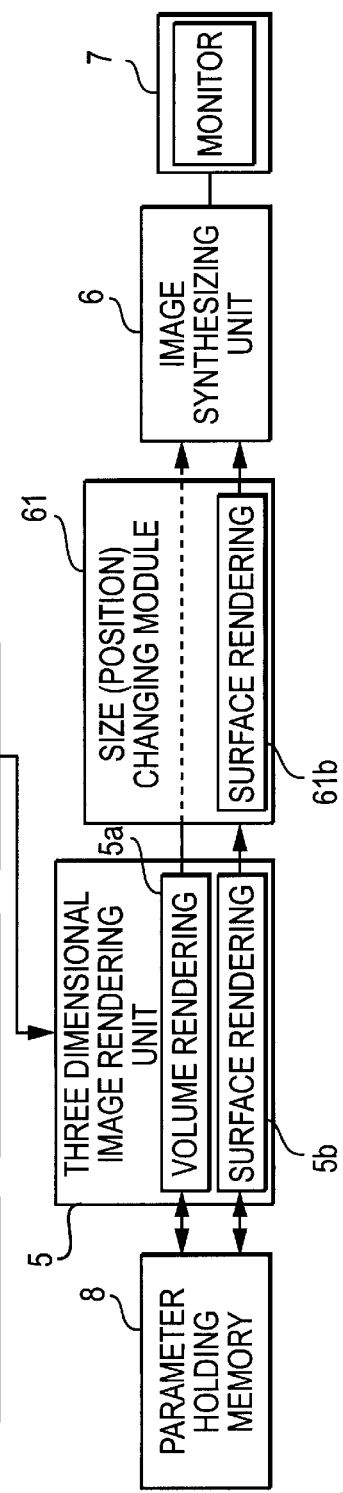
FIGS. 23 and FIG. 24 relate to the third preferred embodiment.

As shown in FIG. 23, according to the present embodiment, a size (position) changing module 61 is interposed between the three-dimensional image rendering unit 5 and image synthesizing unit 6. The size changing module 61 has a surface-mode size (position) changing module 61a for changing the size and display position of surface-rendering data. The other components are identical to those of the first embodiment.

(Operation)

Figure 24:
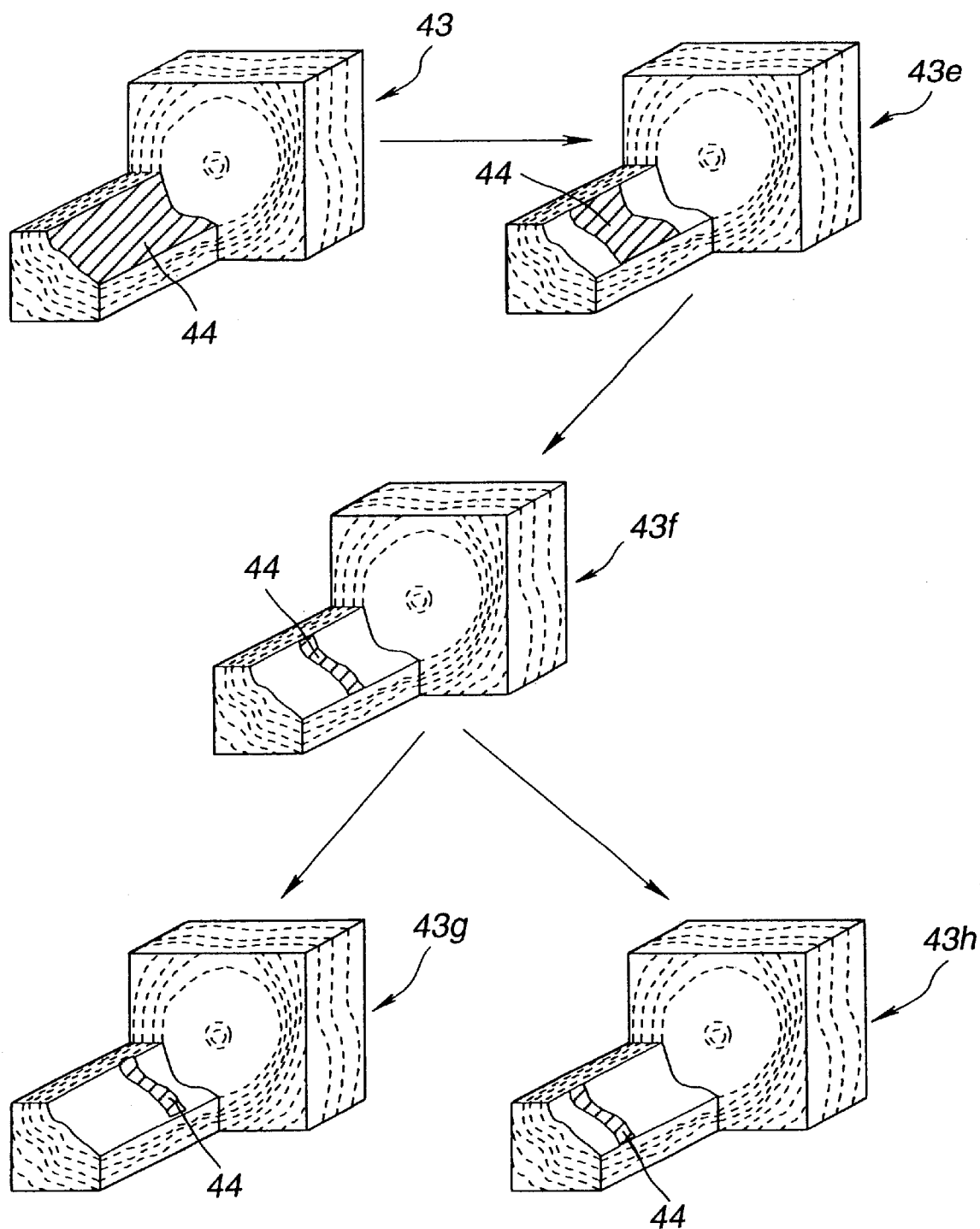

As shown in FIG. 24, according to the present embodiment, a pointing device such as a mouse (not shown) is used to shrink the surface-rendering data 44 and to thus convert the initial three-dimensional image 43 into a three-dimensional image 43e.

Moreover, the three-dimensional image 43e may be converted into a three-dimensional image 43f having the surface-rendering data 44 shrunk further.

Moreover, the point device is used to move the shrunkened surface-rendering data 44 to a deeper position and to thus convert the three-dimensional image 43f into a three-dimensional image 43g. Likewise, the shrunkened surface-rendering data 44 may be moved to a forward position and the three-dimensional image 43f may thus be converted into a three-dimensional image 43h. The other operations are identical to those of the first embodiment.

(Advantage)

The present embodiment can provide the same advantages as the first embodiment. In addition, the surface-rendering data 44 can be changed in size or position. Consequently, information of minute irregularities on a surface can be visualized using surface-rendering data, and an internal state can be visualized using volume-rendering data.

Fourth Embodiment (Constituent Features)

The fourth embodiment is substantially identical to the first embodiment. As such, only the difference will be described. The same reference numerals will be assigned to identical components, and the description of these components will be omitted.

Figure 25:
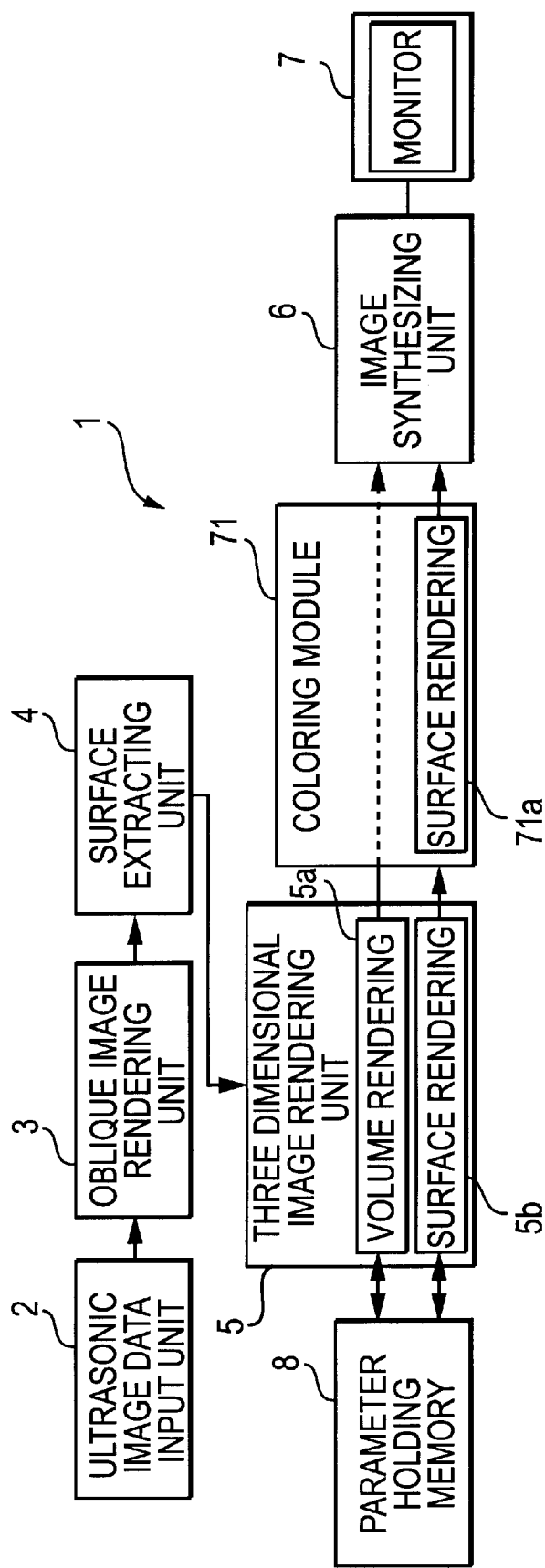
FIGS. 25 to FIG. 27 relate to the fourth preferred embodiment.

As shown in FIG. 25, according to the present embodiment, a coloring module 71 having a surface-mode coloring module 71a for coloring surface-rendering data is interposed between the three-dimensional image rendering unit 5 and image synthesizing unit 6.

(Operation)

Figure 26:
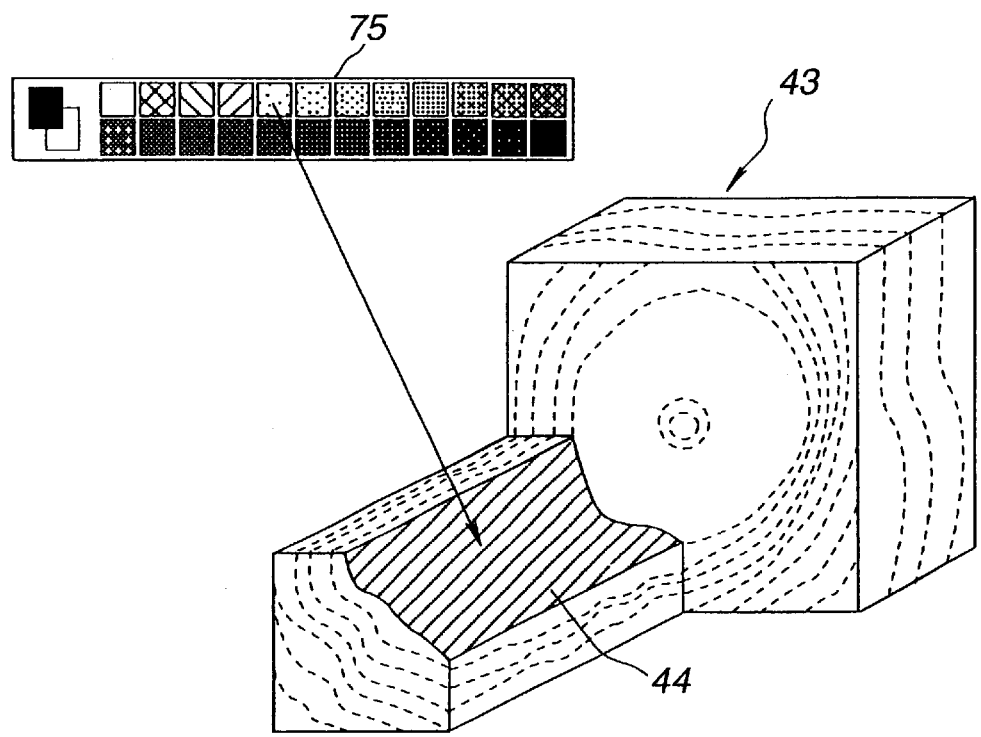

According to the present embodiment, a pointing device such as a mouse (not shown) is used to select colors from a color palette 75 as shown in FIG. 26. The three-dimensional image 43 including the surface-rendering data 44 is thus colored.

Figure 27:
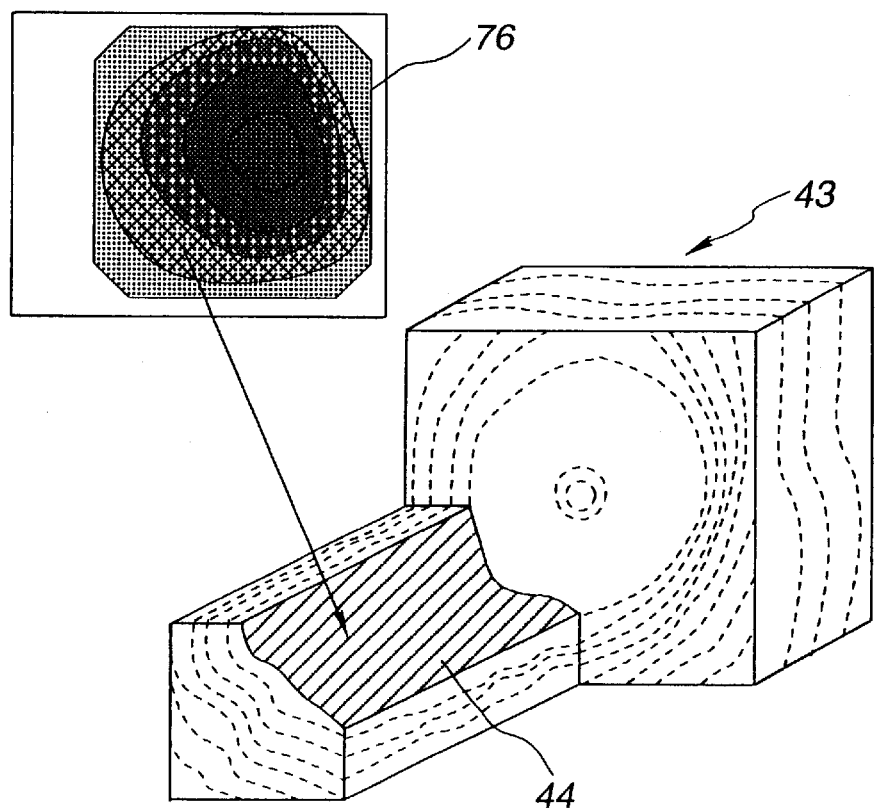

Referring to FIG. 27, the pointing device is used to color the three-dimensional image 43 including the surface-rendering data 44 according to color data obtained from an endoscopic image 76. The other operations are identical to those of the first embodiment.

(Advantage)

As mentioned above, the present embodiment provides the same advantages as the first embodiment. In addition, since the three-dimensional image 43 can be colored, an organ or tumor that is hard to identify in a gray-scale imaging mode can be identified readily. Moreover, data obtained from an endoscopic image (image data produced by an endoscope used during an ultrasonic examination) can be adopted as color data. A more realistic image can be produced.

According to the present invention, it is apparent that a wide range of different embodiments can be constructed based on the invention without departing from the spirit and scope of the invention. The present invention will be limited to the appended claims but not restricted by any specific embodiment described herein.

What is claimed is:

1. An ultrasonic image processing apparatus, comprising:

an ultrasonic data acquiring unit for acquiring ultrasonic data of an intracavitary region;

an oblique image producing unit for producing an oblique image of a section of the intracavitary region; and a three-dimensional image rendering unit for extracting section data from the oblique image and the ultrasonic data of a intracavitary wall of the intracavitary region and thus producing a three-dimensional image.

2. An ultrasonic image processing apparatus according to claim 1, wherein said three-dimensional image rendering unit arbitrarily changes a position of the section of the oblique image and a viewing angle of the oblique image so as to produce a three-dimensional image.

3. An ultrasonic image processing apparatus according to claim 1, wherein said three-dimensional image rendering unit comprises:

a volume-mode image rendering unit for rendering a three-dimensional image using volume-rendering data;

a surface-mode image rendering unit for rendering a three-dimensional image using surface-rendering data; and a display unit for alternately or concurrently displaying the three-dimensional image of volume-rendering data and the three dimensional image of surface-rendering data.

4. An ultrasonic image processing apparatus according to claim 3, wherein said volume-mode image rendering unit and surface-mode image rendering unit can mutually independently set a transmittance for producing a three-dimensional image.

5. An ultrasonic image processing apparatus according to claim 3, wherein said surface-mode image rendering unit can set a size and position of the three-dimensional image of surface-rendering data.

6. An ultrasonic image processing apparatus according to claim 3, wherein said surface-mode image rendering unit can color the three-dimensional image using a color palette or medical image.

7. An ultrasonic image processing apparatus according to claim 1, further comprising a synthesizing unit for synthesizing the three-dimensional image of volume-rendering data and the three-dimensional image of surface-rendering data.

8. An ultrasonic image processing apparatus according to claim 7, wherein said volume-mode image rendering unit and surface-mode image rendering unit can mutually independently set a transmittance for producing a three-dimensional image.

9. An ultrasonic image processing apparatus according to claim 7, wherein said surface-mode image rendering unit can set a size and position of the three-dimensional image of surface-rendering data.

10. An ultrasonic image processing apparatus according to claim 7, wherein said surface-mode image rendering unit can color the three-dimensional image using a color palette or medical image.

11. An ultrasonic image processing method, comprising:

an ultrasonic data acquiring step of acquiring ultrasonic data of an intracavitary region;

an oblique image producing step of producing an oblique image at a section of the intracavitary region; and a three-dimensional image rendering step of extracting section data from the oblique image and the ultrasonic data of an intracavitary wall of the intracavitary region so as to produce a three-dimensional image, wherein at said three-dimensional image rendering step, the data of the intracavitary wall is extracted based on a length of a vector extending from a viewing plane from which an observer would view the three dimensional image which is limited by the oblique image to a point along the vector at the three-dimensional image.

12. An ultrasonic image processing method according to claim 11, wherein said observer's eye may be located at an infinite distance from the oblique image.

13. An ultrasonic image processing method according to claim 11, wherein at said three-dimensional image rendering step, the three-dimensional image is produced by arbitrarily changing a position of the section of the oblique image and a viewing angle of the oblique image.

14. An ultrasonic image processing method according to claim 11, wherein said three-dimensional image rendering step comprises:

a volume-mode image rendering step of producing a three-dimensional image using volume-rendering data, a surface-mode image rendering step of producing a three-dimensional image using surface-rendering data, and a display step of alternately or concurrently displaying the three-dimensional image of volume-rendering data and the three-dimensional image of surface-rendering data.

15. An ultrasonic image processing method according to claim 14, wherein at each of said volume-mode image rendering step and surface-mode image rendering step, a transmittance can be set for producing a three-dimensional image.

16. An ultrasonic image processing method according to claim 14, wherein at said surface-mode image rendering step, a size and position of the three-dimensional image of surface-rendering data can be set.

17. An ultrasonic image processing method according to claim 14, wherein at said surface-mode image rendering step, the three-dimensional image can be colored using a color palette or medical image.

18. An ultrasonic image processing method according to claim 11, further comprising a synthesizing step of synthesizing the three-dimensional image of volume-rendering data and the three-dimensional image of surface-rendering data and displaying a resultant three-dimensional image.

19. An ultrasonic image processing method according to claim 18, wherein at each of said volume-mode image rendering step and surface-mode image rendering step, a transmittance can be set for producing a three-dimensional image.

20. An ultrasonic image processing-method according to claim 18, wherein at said surface-mode image rendering step, a size and position of the three-dimensional image of surface-rendering data can be set.

21. An ultrasonic image processing method according to claim 18, wherein at said surface-mode image rendering step, the three-dimensional image can be colored using a color palette or medical image.

* * * * *